(12) United States Patent
Schwoebel et al.

(10) Patent No.: US 11,534,118 B2
(45) Date of Patent: Dec. 27, 2022

(54) STATIONARY X-RAY SOURCE

(71) Applicants: The Regents of the University of California, Oakland, CA (US); SRI International, Menlo Park, CA (US)

(72) Inventors: Paul R. Schwoebel, Bosque Farms, NM (US); John M. Boone, Fair Oaks, CA (US)

(73) Assignees: The Regents of the University of California, Oakland, CA (US); SRI International, Menlo Park, CA (US)

( * ) Notice: Subject to any disclaimer, the term of this patent is extended or adjusted under 35 U.S.C. 154(b) by 21 days.

(21) Appl. No.: 17/338,299

(22) Filed: Jun. 3, 2021

(65) Prior Publication Data
US 2021/0338181 A1 Nov. 4, 2021

Related U.S. Application Data

(62) Division of application No. 16/089,672, filed as application No. PCT/US2017/025497 on Mar. 31, 2017, now Pat. No. 11,123,027.
(Continued)

(51) Int. Cl.
*A61B 6/00* (2006.01)
*H01J 35/14* (2006.01)
(Continued)

(52) U.S. Cl.
CPC .............. *A61B 6/4021* (2013.01); *A61B 6/06* (2013.01); *A61B 6/4007* (2013.01);
(Continued)

(58) Field of Classification Search
CPC ....... A61B 6/4021; A61B 6/06; A61B 6/4007; A61B 6/4035; A61B 6/025; A61B 6/502;
(Continued)

(56) References Cited

U.S. PATENT DOCUMENTS 4,405,876 A 9/1983 Iversen
4,592,079 A 5/1986 Sohval et al.
(Continued)

FOREIGN PATENT DOCUMENTS

EP 1028451 A1 8/2000

OTHER PUBLICATIONS

International Application No. PCT/US2017/025497, International Search Report and Written Opinion dated Jun. 21, 2017, 10 pages.

*Primary Examiner* — Marcus H Taningco
(74) *Attorney, Agent, or Firm* — Kilpatrick Townsend and Stockton LLP

(57) ABSTRACT

Embodiments provide a stationary X-ray source for a multisource X-ray imaging system for tomographic imaging. The stationary X-ray source includes an array of thermionic cathodes and, in most embodiments a rotating anode. The anode rotates about a rotation axis, however the anode is stationary in the horizontal or vertical dimensions (e.g. about axes perpendicular to the rotation axis). The elimination of mechanical motion improves the image quality by elimination of mechanical vibration and source motion; simplifies system design that reduces system size and cost; increases angular coverage with no increase in scan time; and results in short scan times to, in medical some medical imaging applications, reduce patient-motion-induced blurring.

20 Claims, 16 Drawing Sheets

Related U.S. Application Data

(60) Provisional application No. 62/316,211, filed on Mar. 31, 2016.

(51) Int. Cl.
| | |
|---|---|
| *A61B 6/06* | (2006.01) |
| *G01N 23/046* | (2018.01) |
| *G01N 23/083* | (2018.01) |
| *G01N 23/10* | (2018.01) |
| *H01J 35/04* | (2006.01) |
| *H01J 35/10* | (2006.01) |
| *A61B 6/02* | (2006.01) |

(52) U.S. Cl.
CPC ......... *A61B 6/4035* (2013.01); *G01N 23/046* (2013.01); *G01N 23/083* (2013.01); *G01N 23/10* (2013.01); *H01J 35/045* (2013.01); *H01J 35/106* (2013.01); *H01J 35/147* (2019.05); *A61B 6/025* (2013.01); *A61B 6/502* (2013.01); *A61B 6/548* (2013.01); *G01N 2223/04* (2013.01); *G01N 2223/3303* (2013.01); *G01N 2223/419* (2013.01); *G01N 2223/639* (2013.01); *H01J 2235/068* (2013.01); *H01J 2235/1204* (2013.01); *H01J 2235/1262* (2013.01)

(58) Field of Classification Search
CPC .... A61B 6/548; G01N 23/046; G01N 23/083; G01N 23/10; G01N 2223/04; G01N 2223/3303; G01N 2223/419; G01N 2223/639; H01J 35/045; H01J 35/106; H01J 35/147; H01J 2235/068; H01J 2235/1204; H01J 2235/1262; H01J 2235/086; H01J 35/10
See application file for complete search history.

(56) References Cited

U.S. PATENT DOCUMENTS

| | | | |
|---|---|---|---|
| 7,065,179 | B2 | 6/2006 | Block et al. |
| 7,881,425 | B2 | 2/2011 | Vermilyea et al. |
| 9,237,872 | B2 | 1/2016 | Tkaczyk et al. |
| 9,490,099 | B2 | 11/2016 | Mackie et al. |
| 2005/0053189 | A1 | 3/2005 | Gohno et al. |
| 2005/0226375 | A1 | 10/2005 | Eberhard et al. |
| 2007/0009081 | A1 | 1/2007 | Zhou et al. |
| 2008/0049902 | A1 | 2/2008 | Holm et al. |
| 2009/0304158 | A1 | 12/2009 | Frutschy et al. |
| 2010/0074392 | A1 | 3/2010 | Behling et al. |
| 2010/0310045 | A1 | 12/2010 | Brown et al. |
| 2011/0051895 | A1* | 3/2011 | Vogtmeier ........... A61B 6/4021 378/92 |
| 2011/0135066 | A1* | 6/2011 | Behling .................. H01J 35/10 378/138 |

\* cited by examiner

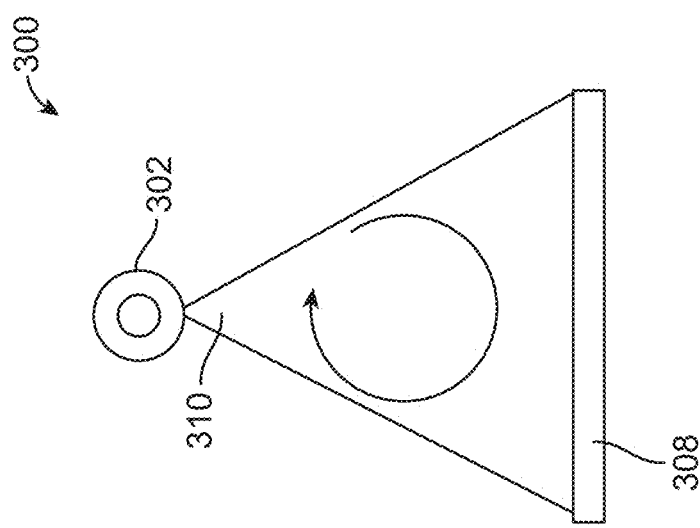
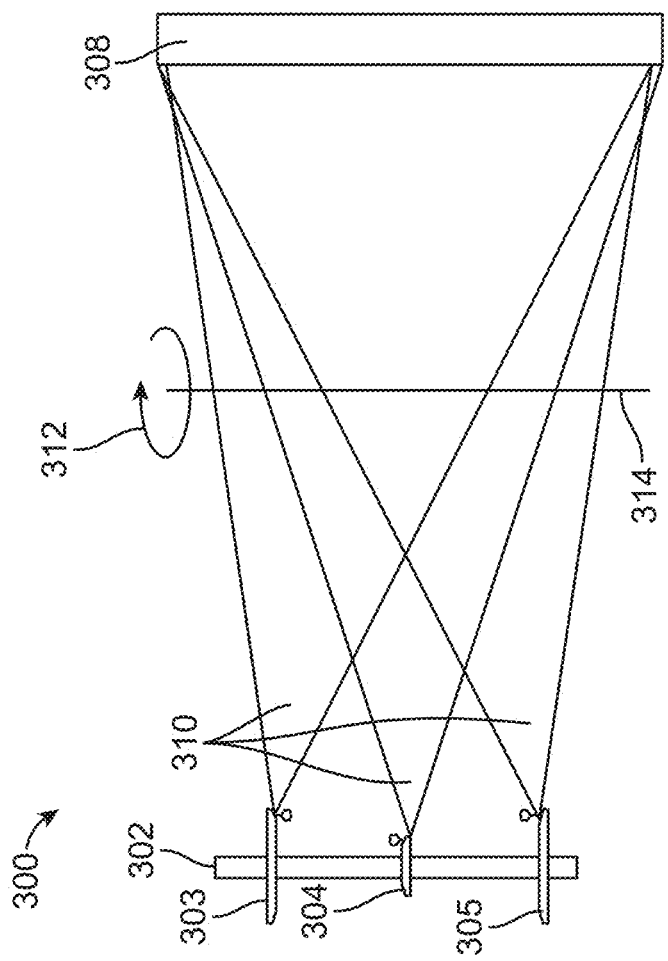
FIG. 6B
FIG. 6A

STATIONARY X-RAY SOURCE

RELATED APPLICATIONS

This application is a divisional application of U.S. application Ser. No. 16/089,672 filed Sep. 28, 2018, which is a US National Phase Application Under 371 of PCT Appln. PCT/US2017/025497 filed Mar. 31, 2017, which claims the benefit of and priority to U.S. Provisional Patent Application No. 62/316,211, entitled "Stationary X-Ray Source," filed on Mar. 31, 2016, the entire disclosures of each of which are incorporated herein by reference for all purposes.

BACKGROUND OF THE INVENTION

Digital breast tomosynthesis (DBT) is a relatively new medical imaging technology with the promise to improve diagnostic accuracy in the early detection of breast cancer. Current systems focus on a stationary X-ray source using field-emission cathodes fabricated from carbon nanotubes, graphene, and metal. Currently, no commercially available stationary source system, DBT or otherwise, is used in a clinical setting, in part because field-emission cathodes are not sufficiently reliable for medical X-ray imaging. This problem has existed since the first attempts to apply the field-emission cathodes to X-ray tubes in the 1920s.

Embodiments of the present invention solve these problems and other problems, individually and collectively.

BRIEF SUMMARY OF THE INVENTION

The present invention provides a stationary multisource X-ray imaging system including a stationary X-ray source for tomographic imaging and a control system for controlling the stationary source. According to some embodiments, the stationary multisource X-ray imaging system may include a tomosynthesis (TS) system. The stationary X-ray source includes at least one stationary multi-X-ray source array and a stationary, but in some embodiments, rotating anode (e.g. a cylindrical, elliptical or spherical anode). The stationary multi-X-ray source array may include a plurality of cathodes such as gridded thermionic cathodes. The rotating anode may include a shaft (e.g. a cylinder) and a plurality of discs coupled to the shaft.

Embodiments provide an X-ray imaging system comprising a stationary source and a control system for controlling the stationary source. The stationary source includes at least one stationary multi-X-ray source array and an anode. In some embodiments, the anode may rotate about a first axis. The stationary multi-X-ray source array includes a plurality of cathodes. In some embodiments, the plurality of stationary cathodes include at least one thermionic cathode. The anode is stationary with respect to a second and third axes perpendicular to the first axis. In some embodiments, an inner flow chamber is provided within the anode. A coolant (such as water) circulates in the inner flow chamber to carry heat away from the anode.

According to various embodiments, the control system fires the plurality of cathodes of the at least one stationary multi-X-ray source array with variable pulse widths and times between pulses. The plurality of cathodes of the at least one stationary multi-X-ray source array are fired based on a predetermined sequence. In some embodiments, heat distribution in the anode may be controlled using the predetermined sequence. According to various embodiments, the plurality of cathodes are grouped into two stationary multi-X-ray source arrays.

In some embodiments, the anode may include a rotating shaft and a plurality of discs coupled to the rotating shaft. At least two of the plurality of discs may have different diameters. Focal spots may be provided on the surface of the plurality of discs such that electrons emitted by the plurality of cathodes hit the focal spots of the anode to generate X-rays. A control grid may be provided between the anode and the at least one stationary multi-X-ray source array. The control grid includes a plurality of focusing cups corresponding to the plurality of focal spots In some embodiments, the X-ray imaging system may also include a collimator for collimating X-rays generated when electrons emitted by the at least one stationary multi-X-ray source array contact the anode, and a filter coupled to the collimator for filtering the X-rays collimated by the collimator.

Embodiments may provide an X-ray imaging system comprising a stationary source, a stationary detector positioned across from the stationary source, and a control system. The stationary source may include at least one stationary multi-X-ray source array including a plurality of cathodes, an anode rotating about a first axis, and a control grid provided between the anode and the at least one stationary multi-X-ray source array. The anode is stationary with respect to a second and third axes perpendicular to the first axis. The control grid includes a plurality of focusing cups corresponding to a plurality of focal spots formed on an exterior surface of the anode. The plurality of focusing cups are configured to direct electrons emitted by the plurality of cathodes toward the plurality of focal spots of the anode to generate X-rays. Projections of an object imaged using the X-ray imaging system are formed on the detector. The control system may be programmed to control the stationary source to fire the plurality of cathodes of the at least one stationary multi-X-ray source array based on a predetermined sequence, acquire the projections from the stationary detector, and reconstruct a 3-D image of the object using the projections acquired from the stationary detector.

In some embodiments, a first cathode among the plurality of cathodes forms a first projection of the object from a first angle, and a second cathode among the plurality of cathodes forms a second projection of the object from a second angle different than the first angle.

These and other embodiments are described in further detail below.

BRIEF DESCRIPTION OF THE DRAWINGS

FIGS. 6A and 6B illustrate elements of a stationary multisource X-ray imaging system, according to various embodiments.

DETAILED DESCRIPTION OF THE INVENTION

Figure 1:
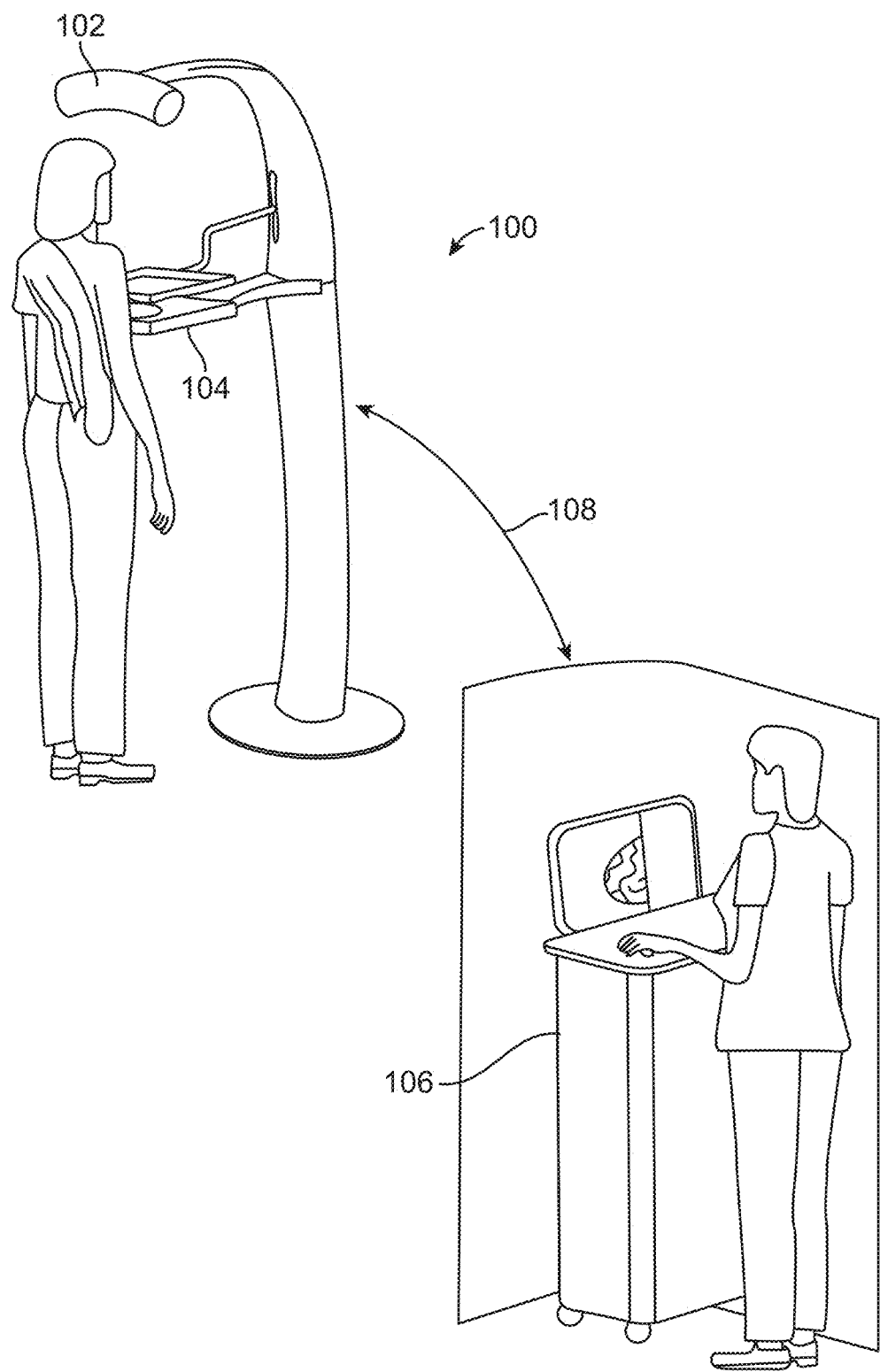
FIG. 1 illustrates a stationary multisource X-ray imaging system, according to various embodiments.

The present invention provides a stationary multisource X-ray imaging system including a stationary X-ray source for tomographic imaging and a control system for controlling the stationary source. According to some embodiments, the stationary multisource X-ray imaging system may include a tomosynthesis (TS) system. The stationary X-ray source includes at least one stationary multi-X-ray source array and a stationary but, in many embodiments, rotating anode (e.g. a cylindrical, elliptical or spherical anode). In some embodiments, the anode may include an anode tube. The stationary multi-X-ray source array may include a plurality of cathodes such as gridded thermionic cathodes. The rotating anode may include a shaft (e.g. a tube) and a plurality of discs coupled to the shaft.

Embodiments provide robust and very high X-ray flux operation. This is accomplished by using an array of thermionic cathodes and a unique rotating anode assembly for power handling. The individual multi-X-ray source array elements are switched on and off sequentially at up to about 200 Hz rates. Each cathode in the array images the object from a different angle. Using the images from different angles, a 3D image of the object is reconstructed. In contrast, with conventional systems, the 3D images can only be constructed when the entire CT scanner is moved around the subject. The stationary multisource design described herein integrates two X-ray tube technologies: an array of thermionic cathodes and an anode. In some embodiments, the anode may include a rotating anode tube. The rotating anode may rotate about a first axis, and the anode may be stationary with respect to a second and third axes perpendicular to the first axis. Embodiments are further directed to measuring X-ray emission characteristics (focal spot, energy distribution, flux); demonstrating high-speed source operation by cycling through the individual source elements at about 200 Hz; performing lifetime measurements; and producing and reconstructing tomographic data.

According to various embodiments, the elements of the array of the stationary multisource X-ray imaging system may be turned on (e.g. fired) sequentially in a row. Alternatively, the elements of the array of the stationary multisource X-ray imaging system may be turned on (e.g. fired) based on a predetermined sequence (e.g. not necessarily in a row). Accordingly, it is possible to get different reconstructed images of moving objects (e.g. heart, blood flow, etc.) using different turn-on sequences. Moreover, different turn-on sequences result in different heat distribution in the anode. Thus, it is possible to improve the heat distribution based on the selected turn-on sequence.

Embodiments provide a versatile X-ray imaging system that uniquely integrates time-proven X-ray tube technologies and enables the construction of higher-resolution X-ray equipment with shorter scan times for the early detection of diseases such as breast cancer, and/or provide high-performance, reliable X-ray imaging systems for applications in abdominal imaging and detection of lung metastases.

Embodiments provide and quantify the performance of a stationary X-ray source and stationary detector, i.e. a stationary-stationary, X-ray imaging system (e.g. a tomosynthesis (TS) system). The elimination of mechanical motion during imaging provides several important advantages over existing systems, including but not limited to (1) improved image quality by elimination of mechanical vibration and source motion, (2) simplified system design that reduces system size and cost, (3) straightforward implementation of increased angular coverage with no increase in scan time, and (4) short scan times to reduce patient-motion-induced blurring.

To that end, embodiments provide a stationary multisource X-ray imaging system based on a novel approach to integrating two technologies used in medical X-ray imaging: an array of thermionic cathodes and a rotating anode. Integrating these technologies results in a reliable, long-lived, highly capable stationary multisource X-ray imaging system with scan times that are factors of 3 to over 10 times shorter than those of commercial tomosynthesis (TS) systems using mechanical source translation. Short scan times are key to exploiting the improved imaging sensitivity of tomosynthesis because they reduce the chance of blurring resulting from patient motion. Embodiments provide short scan times because the X-ray flux exceeds that of conventional stationary-source approaches and conventional tomosynthesis tubes as embodiments use both a rotating anode and multiple X-ray sources (e.g. an array of stationary X-ray sources such as thermionic cathodes, referred herein as "multi-X-ray source array") that fire at different sequences to distribute the thermal load generated in the anode. Because the proposed X-ray imaging system enables straightforward implementation of single-scan dual-energy imaging, a series of scans may be used to quantify contrast agent wash-in/wash-out.

Embodiments are directed to an X-ray imaging system including a stationary source and a control system. The stationary source may include at least one stationary multi-X-ray source array and a rotating anode. The at least one stationary multi-X-ray source array may include a plurality of X-ray sources such as a plurality of thermionic cathodes. The stationary source may also include a collimator coupled to the anode and a filter coupled to the collimator. According to various embodiments, the stationary source is integrated into an X-ray imaging system. For example, the stationary source may be integrated into a design-flexible X-ray imaging system with flat-panel detector and synchronization software (e.g. the control system). An exemplary X-ray imaging system is illustrated in FIG. 1 and the structure of the stationary source is discussed below in greater detail in connection with at least FIGS. 2A-2C.

As illustrated in FIG. 1, a stationary multisource X-ray imaging system 100 may include a stationary X-ray source 102, a stationary detector 104 (e.g. the detector 104 may remain stationary during imaging of the object), and a control system 106. The control system 106 may communicate with the detector 104 and/or the stationary source 102 via one or more of a wire-based or wireless communication technology 108. Examples of wireless communication technology may include communication networks such as a mobile network, a wireless network, a cellular network, a local area network (LAN), a wide area network (WAN), other wireless communication networks, or combinations thereof. According to various embodiments, the stationary detector 104 may be adjusted with respect to the object to be imaged (e.g. the patient, or a body part of the patient). Once positioned, the detector 104 may remain stationary during the imaging process.

The stationary multisource X-ray imaging system 100 illustrated in FIG. 1 may remove mechanical motion during imaging from modern breast X-ray imaging systems. The lack of motion during imaging provides many advantages such as elimination of any possible image blurring effects due to tube movement or vibration, the associated simplified system design and reduction in system size. The simplified system design and reduced size increases reliability and decreases purchase and maintenance costs. Also, a key benefit is the very short scan times. Scan time is one of the more desirable performance metrics for X-ray imaging systems. Scan times need to be short enough to reduce instances of patient motion resulting in image blurring, yet preserve image quality. Because the source described herein has sufficient X-ray flux and scan times that are independent of angular coverage, the result is that scan times will be factors of 3 to over 10 times shorter than existing commercial sources.

Embodiments enable the application of stationary X-ray imaging technology to tomosynthesis (TS) or digital breast tomosynthesis (DBT) by uniquely combining the two technologies of an array of stationary cathodes and a rotating anode to construct an X-ray imaging system with a stationary X-ray source. According to various embodiments, the stationary X-ray source includes at least one array of cathodes and an anode that are both stationary. Even though the anode is stationary in a vertical and horizontal dimension, in some embodiments, the anode may rotate around an axis of rotation (e.g. a central axis of the tube).

The stationary source 102 of the stationary multisource X-ray imaging system 100 is discussed next in greater detail.

Stationary Source

Figure 2A:
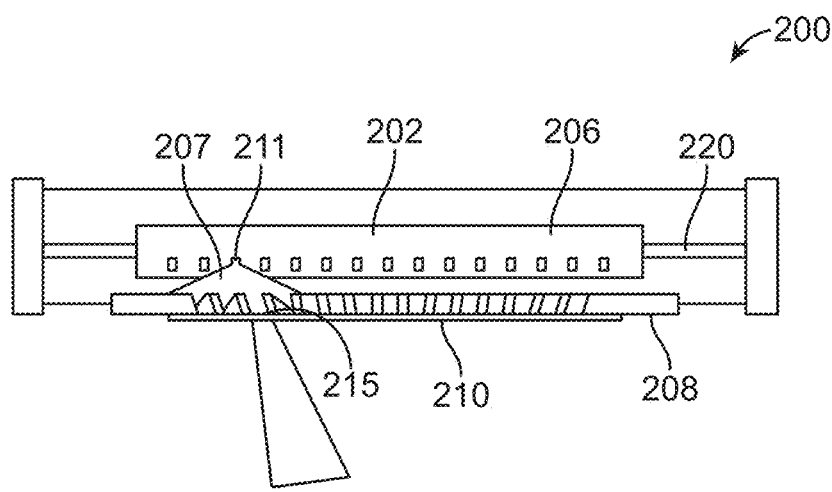
FIG. 2A illustrates a side view of a stationary source of an exemplary multisource X-ray imaging system, according to various embodiments.
Figure 2B:
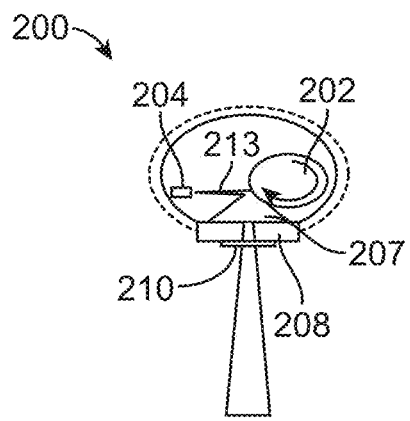
FIG. 2B illustrates an end view of the stationary source of the exemplary multisource X-ray imaging system illustrated in FIG. 2A, according to various embodiments.
Figure 2C:
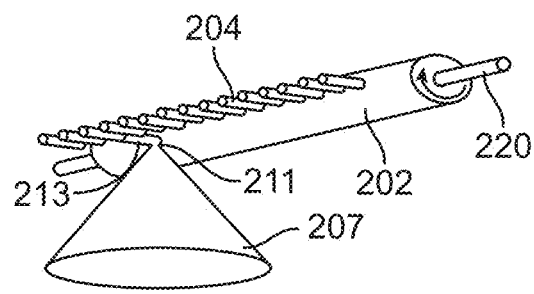
FIG. 2C illustrates a perspective view of an exemplary multisource X-ray imaging system illustrated in FIG. 2A, according to various embodiments.
Figure 2D:
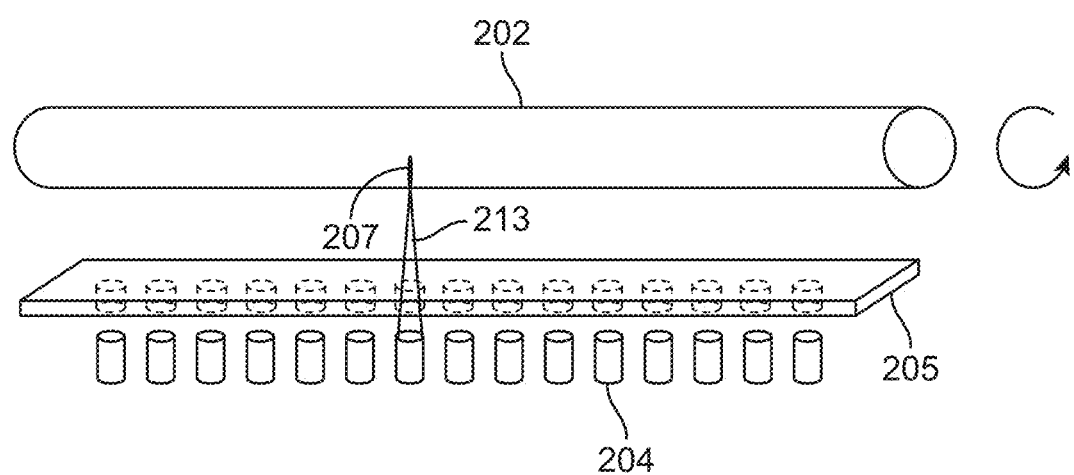
FIG. 2D illustrates elements of the stationary source of the exemplary multisource X-ray imaging system illustrated in FIG. 2A, according to various embodiments.
Figure 2E:
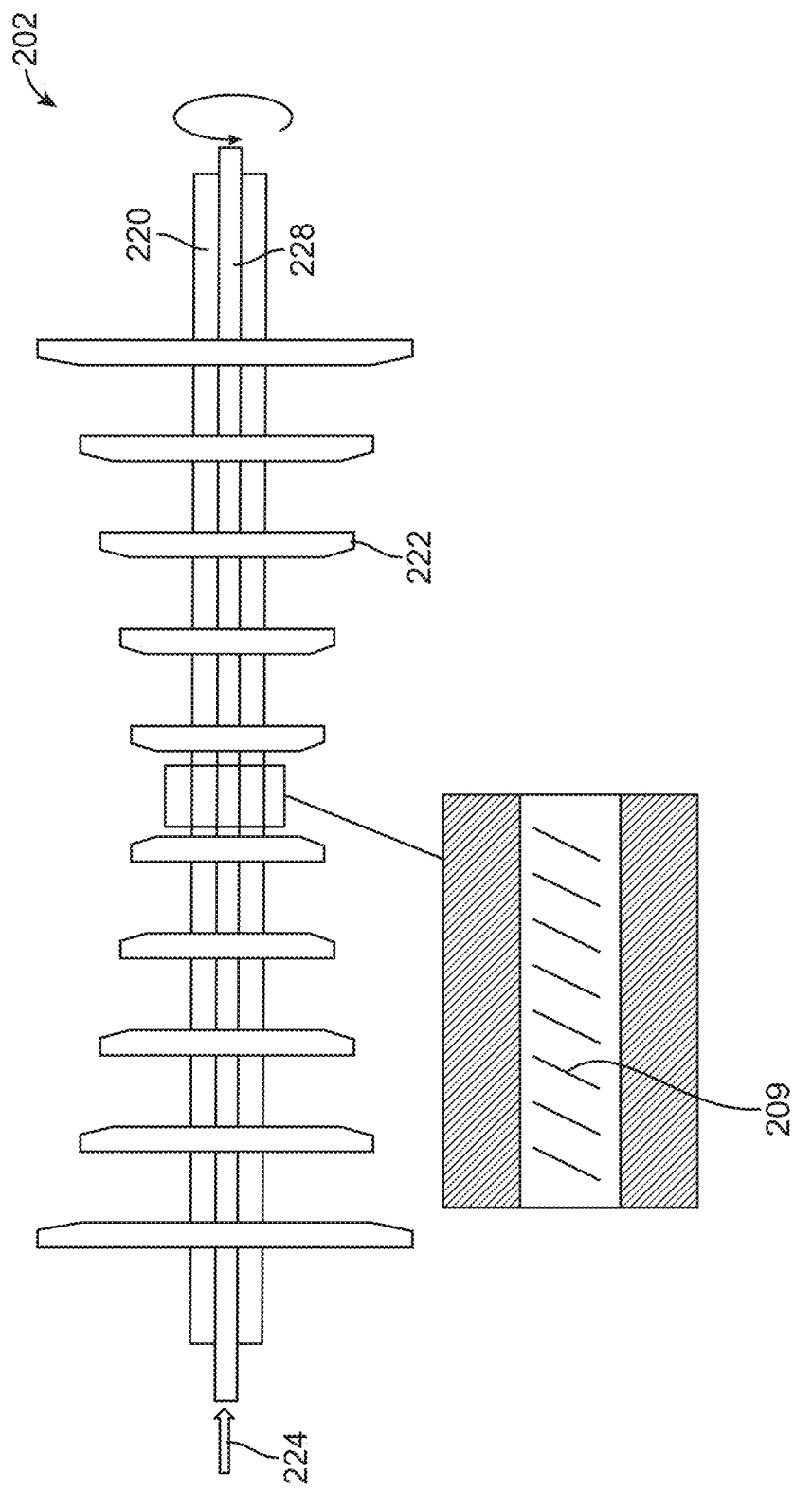
FIG. 2E illustrates the rotating anode of the stationary source of the exemplary multisource X-ray imaging system illustrated in FIGS. 2A-2D, according to various embodiments.

FIGS. 2A-2E illustrate an exemplary stationary X-ray source 200 of the X-ray imaging system 100. Specifically, FIG. 2A illustrates a side view of a stationary source of an exemplary multisource X-ray imaging system, FIG. 2B illustrates an end view of the stationary source, FIG. 2C illustrates a perspective view of the stationary source, FIG. 2D illustrates elements of the stationary source, and FIG. 2E illustrates the rotating anode of the stationary source.

As illustrated in FIGS. 2A-2E, the stationary X-ray source 200 includes at least one stationary multi-X-ray source array 204 and a stationary but rotating anode 202. That is, the anode rotates about a first axis (i.e. the rotation axis) but the anode is stationary with respect to a second and third axes perpendicular to the first axis (i.e. the anode is stationary in the vertical and/or horizontal dimensions). The stationary multi-X-ray source array 204 may include a plurality of cathodes such as gridded thermionic cathodes. The rotating anode 202 may include a shaft (e.g. a tube) 220 and a plurality of discs 222 coupled to the shaft (illustrated in FIG. 2E).

In the stationary X-ray source 200, the array of thermionic cathodes 204 (e.g. tungsten filament cathodes) are provided opposite from the rotating anode 202. The rotating anode 202 may be a cylindrical anode. One of ordinary skill in the art would appreciate that the anode is not limited to a cylindrical shape but can have an elliptical, spherical, etc. shape as well. The electrons generated at the cathodes 204 speed up toward and hit the anode 202 creating the X-rays 207. The electron beam spots 206 illustrated on the surface of the anode 202 are where the X-rays 207 are generated. The generated X-rays 207 are then guided by a collimator 208 (provided across from the anode 202) toward the subject that is being imaged (e.g. the collimator 208 is positioned between the anode 202 and the subject). The collimator 208 may be a lead or tungsten collimator 208 composed of a set of apertures to collimate the X-ray beam 207 from each source element 204. The design of the collimator 208 may depend on the subject being imaged and/or the imaging requirements. In FIG. 2A, only the X-rays that are being guided by the collimator 208 are illustrated. One of ordinary skill in the art would appreciate that the X-rays are generated isotopically and radiate in all directions in addition to the direction illustrated in FIG. 2A.

For example, in the embodiment illustrated in FIG. 2A, the focal spot #3 (third electron beam spot 211 from the left) is hit by the electrons 213 generated at the cathodes 204 (illustrated in FIGS. 2B and 2C). The opening on the collimator 208 that corresponds to the focal spot #3 211 (e.g. the third opening 215 from the left on the collimator 208) lets the incoming X-ray beam out toward the subject being imaged.

A grid-controlled cinefluoroscopy-type tube design using a focusing-cup grid 205 (illustrated on FIG. 2D) defines the beam spot (i.e., X-ray focal spot) size on the anode 202 and allows individual multi-X-ray source array elements (e.g. individual cathodes 204) to be turned on (e.g. fired) and turned off at up to about 200 Hz, a frequency far greater than any foreseen for high-speed TS. The focusing-cup grid 205 may include a voltage-controlled focus cup grid for turning on and off each cathode at frequencies up to 200 Hz thereby controlling the firing of the individual cathodes. According to various embodiments, the focusing-cup grid 205 may be provided in the form of an electrode at a specific location between the cathode 204 and the anode 202 (e.g. a cup for each individual focal spot 206 of the anode 202). The focusing-cup grid 205 is an exemplary control grid including both a focus cup and a grid. In some embodiments, the control grid may be formed of a focus cup. The grid may turn on/off the focal spot (e.g. by preventing electrons from flowing between the cathode and the anode with a slight negative potential). The focusing cup may shape the electron cloud for a more desirable focal spot shape (i.e. when the electrons hit the anode the electrons produce the actual "focal spot").

A constant filtration of the X-ray beam is common for standard tomosynthesis operation. The stationary X-ray source 200 of the imaging system may also include a filter 210 coupled to the collimator 208 provided opposite from the anode 202. For example, a tungsten anode with 0.7 mm of aluminum filtration may be used. In some embodiments, a 1-mm thick glass window may be used to approximate the filtration characteristics of 0.7 mm of Al. According to various embodiments, different filter combinations may be used to achieve dual-energy subtraction for specific contrast agents. Dual energy imaging may refer to generating a quick image using all sources (for example at 35,000 V) and then changing the voltage between the anode and the cathodes (for example to 50,000 V). Another image may be generated using the new voltage. By displaying these two images simultaneously or in rapid succession, different information may be gathered. For example, when imaging bones, more bone or more tissue may be displayed/imaged using this technique.

In some embodiments, the multi-X-ray source elements (e.g. cathodes 204) may be provided in form of a plurality of arrays. For example, the multi-X-ray source elements (e.g. cathodes 204) may be formed of two sets of arrays. In some embodiments, the two sets of arrays may be offset with respect to each other. If such exemplary source setup is used for dual-energy imaging, a first array may be kept at a first voltage (e.g. 35,000 V) while second array may be kept at a second voltage. (e.g. 50,000 V). Accordingly, the need to change the voltage between two images may be eliminated.

Table 1 shows the scan parameters of some commercial systems and how they compare with the proposed stationary source X-ray imaging system. Each thermionic cathode supplies sufficient tube current (e.g., up to 200 mA) to provide very short scan times (so short, in fact, that the download time of the detector is currently a significant fraction of the scan time).

TABLE 1

Existing Commercial DBT systems compared with the claimed stationary source system. (For scan times, a 150-mAs exposure and Perkin-Elmer Dexela 2923 detector at full resolution was assumed for the claimed stationary source.)

| Manufacturer/ Model | Scan Angle (deg.) | Number of Projections | Scan Time (s.) | X-Ray Tube Operation | TS Reconstruction Algorithm | US FDA Approved |
|---|---|---|---|---|---|---|
| Hologic Dimensions 3D | 15 | 15 | 3.7 | Continuous sweep pulsed on & off | Filtered back projection (FBP)-based | YES |
| GE/SenoClaire | 24 | 9 | 7-10 | Step and shoot | Iterative | YES |
| Giotto/Giotto Tomo | 40 | 13 | 12 | Step and shoot | Iterative | NO |
| Siemens/ MAMMOMAT Inspiration | 50 | 25 | 20 | Continuous sweep pulsed on & off | FBP-based | NO |
| Proposed stationary source DBT system | 15<br>24<br>40<br>50 | 15<br>9<br>13<br>25 | 1.3<br>1.1<br>1.3<br>1.7 | Stationary | Iterative, FBP, and matrix inversion tomosynthesis will be compared | N/A |

The existing commercial systems shown in Table 1 mechanically translate a single X-ray source through space and typically trade improvements in image quality that can come from increased angular coverage and increased projection number with an associated increase in scan time. Shorter scan times can be achieved by moving the X-ray tube through space more quickly. However, if the motion is continuous during each exposure, the acceptable degree of X-ray focal spot blurring due to the tube motion during the exposure limits the speed. If the tube is stopped during the exposure, the so-called "stop-and-shoot" approach, scan time limitations are associated with physically accelerating and decelerating the tube. The stationary source described herein has scan times that are 3 to over 10 times shorter than the mechanical systems (see Table 1), and the scan time is independent of the angular coverage.

There is emerging data showing that some scan angle/projection number combinations may provide different detection performance than others. For example, breast microcalcifications may be best detected using small scan angles, whereas tumor-sized objects may be best detected using larger scan angles. The stationary multisource X-ray imaging system described herein can incorporate the capability of an operator-selected scan angle/projection number combination and thereby provide a highly versatile X-ray imaging system with performance that can be tailored to the imaging application.

FIG. 2E illustrates the anode 202 of the stationary multi-X-ray source array imaging system 100. The anode includes a rotating shaft 220 and a plurality of discs 222 coupled to the rotating shaft 220. According to various embodiments, the anode 202 may have an inner flow chamber 228 where a coolant 224 (e.g. high boiling point coolant) circulates to carry the heat away from the rotating anode 202. As illustrated in FIG. 2E, the anode 202 of the stationary multi-X-ray source array imaging system 200 is a long shaft, and the inner flow chamber 228 is a rifled (angled lines 209 illustrating the grooves on the anode 202) tube extending along the shaft 220. Embodiments may line-focus the beam into grooves 209 cut into the anode 202 for some natural collimation along the rotational axis of the cylinder 220. The structure illustrated in FIG. 2E improves heat sinking of the beam power. The spiral scoring on the inside of the inner flow chamber 228, coupled with the extremely fast rotation of the shaft 220 (e.g. at about 3000 to about 10,000 rpm.) and the inertia of the coolant 224, would provide fluid flow through the inner flow chamber 228 (e.g. inner cooling tube) without requiring a separate pump to circulate the coolant 224. The velocity of fluid flow may be determined by the specific angles and depth of the spiral markings 209.

According to some embodiments, the exemplary stationary source 200 illustrated in FIG. 2A may have the following operating parameters: tube voltage 35-50 kV; tube current 200 mA maximum per source-element; X-ray focal spot size 0.3 mm; scan time 1.5 s (limited by detector readout time) at a total exposure (split between 15 source elements) of up to 200 mAs; 15 projections over a 15° scan angle; source-to-image distance (SID) 70 cm; and source-to-object distance (SOD) 65 cm. The control system may have the following operating parameters: Individual X-ray source on-time 5 to 200 ms; and readout of 15 detector frames in 2 s (at full resolution). The filtered back-projection, iterative reconstruction, and matrix-inversion tomosynthesis reconstruction algorithms may be used with the X-ray imaging system for comparison.

As provided above, the stationary source includes at least one stationary multi-X-ray source array that includes multiple stationary cathodes and a stationary but rotating anode. When designing the stationary source, among the first choices to be made are the scan parameters. Scan parameters in tomosynthesis are evolving as trade-space and optimization studies continue. The stationary source described herein significantly increases the available scan parameter space by providing short scan times with both large (>60°) and small (<15°) angular coverages with projection angular separations (i.e., multi-X-ray source array element separations) easily down to 1°. These combined parameters exceed any foreseeable X-ray imaging system needs. The stationary source described herein may be built so as to essentially eliminate the need for scan parameter trade-offs by making available an anode length that can accommodate the largest scan angles, and by allowing an operator-selected scan angle and projection number (i.e., number of individual source elements to be used).

Figure 3A:
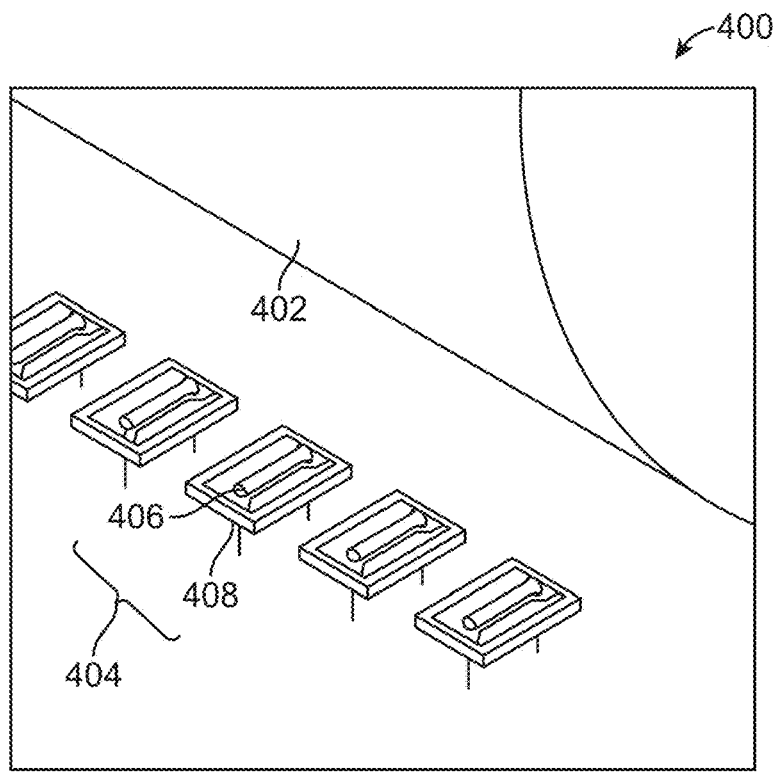
FIGS. 3A-3B illustrates an exemplary stationary X-ray source of an exemplary multisource X-ray imaging system, according to various embodiments.
Figure 3B:
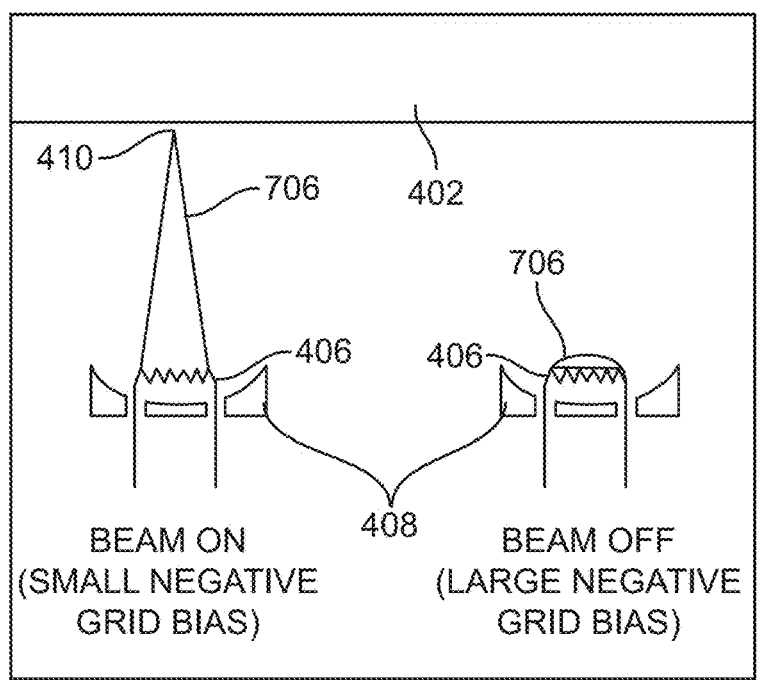

FIGS. 3A and 3B illustrate an exemplary stationary X-ray source 400 including a cylindrical rotating anode 402 and a plurality of cathodes 404. Each cathode 404 includes a tungsten filament 406 and a focus cup grid 408. Tungsten filaments 406 are the most widely used cathodes in X-ray tubes because they are simpler, more reliable and robust, and less expensive than any other type of cathode. As discussed below, their size, power requirements, and associated beam control grid (e.g. focus-cup-grid electrodes) present no issues to their use in a stationary-source X-ray imaging system.

The cathode 404 formed as a tungsten filament and focus-cup-grid assembly provides an effective 0.3 mm focal spot as necessary for TS. The dimensions may accommodate a linear individual source-element density of 2 sources/cm (2 per 1° at a source-to-object distance (SOD) of 65 cm) defined by the minimum size of adjoining focus-cup grids 408. This exceeds any source density anticipated for foreseeable X-ray imaging systems given typical angular coverage/projection number combinations for tomosynthesis in general and in existing and proposed DBT, in particular (see Table 1). With the filaments 406, 24 W of power may be required for a tube current of 200 mA. For an exemplary system including 15 sources, the total power associated with all sources is therefore 360 W, which is roughly equivalent to the maximum power of a common household, incandescent task-lamp. Heat loads associated with such low powers will not adversely impact system performance as a result of issues such as thermal expansion or lack of thermal equilibrium due to intermittent use.

The filaments 406 may be recessed in focus-cup grids 408 as shown in FIG. 3A. The focus-cup grids 408 serve as an element in an electrostatic lens that controls the size of the electron beam 410 on the anode 402. The focus-cup grid 408 for each individual source element 404 (e.g. tungsten filament cathode 406) in the stationary source 400 will have an independently controlled voltage separate from the filament voltage. This design allows the focus-cup grid 408 to be used to turn the electron beam 410 on-and-off and yields what is called a "grid-controlled" or "grid-biased" tube.

Referring now to FIG. 3B, the operation of focus-cup grid control is described next. With a small (e.g. about −200 V) bias on the focus-cup grid 408 with respect to the filament 406, the emitted electrons are focused into a spot on the anode 402 and create X-rays. With a larger bias (e.g. about −2 kV) on the focus-cup grid 408, the electrons are driven back to the filament 406 and no X-rays are produced. According to various embodiments, high-voltage MOSFET transistors may be used to produce the voltage pulses to operate the multi-X-ray source array elements.

A rotating anode 402 is used as a cylinder to produce sufficient X-ray flux and fluence for practical image acquisition times. This new approach allows for the incorporation of a rotating anode 402 into a stationary source 400 to enable the high fluxes required for medical imaging applications. Although a stationary source naturally distributes the beam power over different spots (e.g. 15 spots corresponding to 15 source elements in the exemplary embodiments illustrated in FIGS. 2A-2D) on the anode 402, a stationary anode would still be damaged by overheating as a result of the power required to produce exposures of 100 mAs to 200 mAs with acceptable image acquisition times. Acceptable image acquisition times may require the use of a rotating anode, even for a stationary source with tens of source elements. For DBT, a 34-ms exposure/source element may be required for a 100 mAs exposure and a 67-ms exposure/source element at 200 mAs using 15 source elements (=[100 mAs to 200 mAs]/(200 mA/source element/15 source elements)). The Varian RAD-73 mammography tube (W/Re target) with a 0.3-mm focal spot (anode angle of 16o) has a 4"-diameter anode and can safely handle 200 mA at 45 kVp (greater than the kVp typically used for DBT) with a 200-ms exposure time. Thus a 4" cylindrical rotating anode can easily handle the powers necessary to provide short scan times (e.g. scan times are so short that a significant fraction thereof is the detector download time).

The cylindrical rotating anode 402 may be built using stainless-steel vacuum hardware that can be disassembled as necessary. The X-ray window may be 1-mm-thick borosilicate glass, equivalent to about 0.7 mm of Al at X-ray energies of interest. This may allow to see inside the system to diagnose potential problems (e.g., voltage breakdown). According to some embodiments, metal filters may be inserted between the anode and object to be imaged. Electrical feedthroughs to the individual X-ray source elements (e.g. cathodes) may be provided for both the filaments 406 and focus-cup grids 408 (illustrated in FIG. 5A).

To calculate scan times for the exemplary stationary source 400 described herein, a high-resolution mammography-grade detector that operates at 26 frames/s (fps) with full resolution (1×1 binning) may be used. Then 0.58 s (15 frames/26 fps) may be used to download the 15 exposures of the stationary source. As the stationary source may require 0.5 s to complete a 100-mAs exposure and 1.0 s to complete a 200-mAs exposure using 200-mA/source-element, the scan time is 1.1 s for a 100-mAs exposure and 1.6 s for a 200-mAs exposure. These scan times are roughly 3 to over 10 times shorter than commercial sources providing nominal 100-mAs scans for 'typical' breasts.

Figure 4:
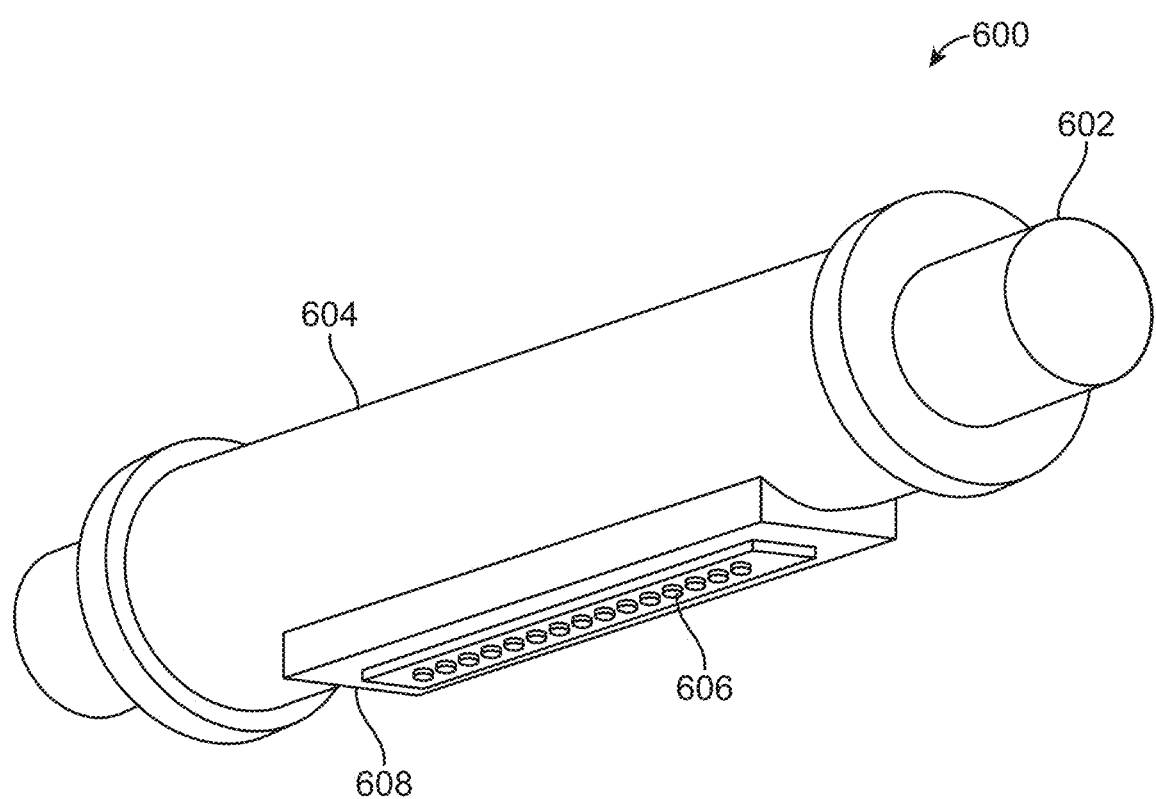
FIG. 4 illustrates a stationary X-ray source containing a rotating anode of an exemplary stationary X-ray source, according to various embodiments.

An exemplary anode assembly 600 for containing the rotating anode is illustrated in FIG. 4. The anode assembly 600 may include a vacuum housing 604 containing the stationary source and an induction motor housing 602 for containing the rotating anode (e.g. cylindrical rotating anode 402 illustrated in FIGS. 3A-3B). The rotating anode may be mounted on custom-built rotor assemblies to be electrically isolated to allow the anode to operate at high voltage. A collimator 608 may be mounted directly on an exterior surface of the vacuum housing 604. The collimator 608 may collimate the X-rays emitted from the rotating anode. A filter 606 (e.g. a beam filter) may be provided at the output of the collimator 608 for filtering the beams collimated at the collimator 608.

Exemplary embodiments may include a hollow (e.g. may not be solid), 4" diameter rotating anode cylinder made from tungsten. Other exemplary rotating anode designs may have a combination of tungsten and rhenium on molybdenum with a graphite backing. The anode may be driven by an induction motor. A rotor may be mechanically connected to the cylindrical anode and attached to the vacuum chamber with a voltage-insulated vacuum feedthrough. The opposite end of the anode may be supported by a second rotor assembly. In some embodiments, a stator may be needed as the anode may be driven from one end only. With the cylindrical rotating anode, the source-to-object distance (SOD) varies with a cosine distribution and the entrance dose on the object may be kept constant by electrically adjusting the individual current (mA) of each source element.

Figure 5A:
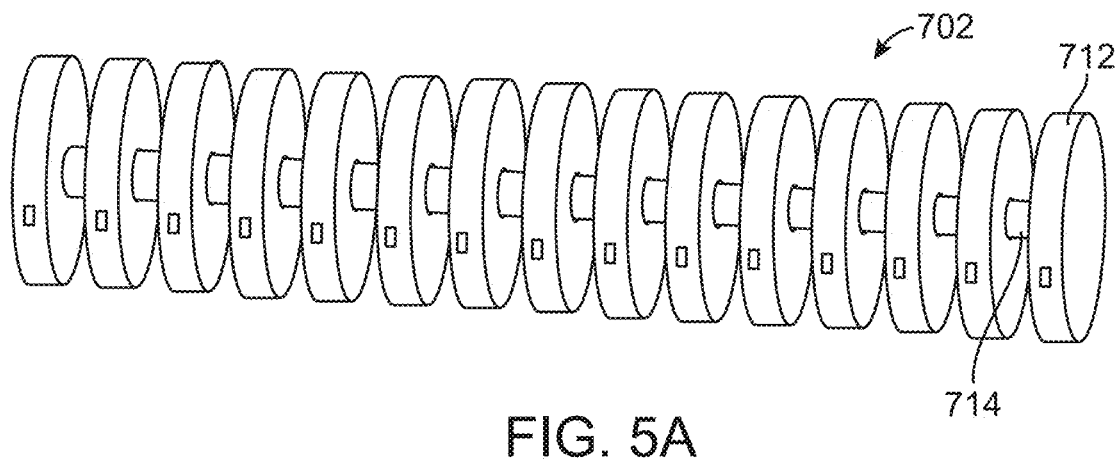
FIGS. 5A and 5B illustrate exemplary rotating anodes, according to various embodiments.
Figure 5B:
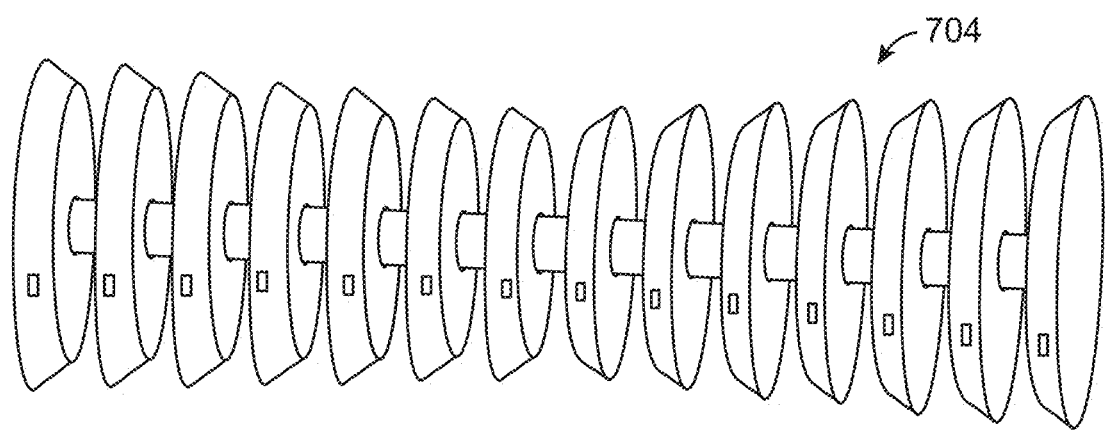

FIGS. 5A and 5B illustrate two exemplary anode designs 702 and 704, respectively. In FIG. 5A, the anode 702 is made from, for example, tungsten discs of two different diameters 712 and 714. The individual beams from the stationary source strike the anode 702 on the discs with the larger diameter 712. This anode design reduces weight and enhances the radiative cooling rate due to the increase in anode surface area relative to that of the plain cylinder anode.

FIG. 5B illustrates a variation where the anode 704 includes stacked disks having diameters that gradually increase from the center to the ends of the anode 704 and have a face cut at a fixed angle relative to the axis of rotation to mechanically rotate the focal spot to face the object center. This design may allow a constant X-ray focal spot size and source-to-object distance (SOD) to be maintained as the stationary sources are scanned while still providing for the use of a simple, cylindrically symmetric vacuum chamber for the stationary sources. The X-ray focal spot (sizes/shapes may be individually tailored by adjusting the voltages on the individual focus-cup grids) position on the anode 704 would be farther from the rotational axis of the anode closer to the edges of the anode 704 in order to keep constant SOD (i.e., emulate the path a single X-ray tube travels in an arc). The filaments may be spatially located on a compound curve. The structure may result in simplification of the reconstruction algorithm and prevention of image artifacts. The mechanical rigidity of the configuration illustrated in FIG. 5B eliminates errors in source position (e.g. along the arc of travel), which may occur due to pulse-timing-synchronization issues in a mechanically swept system.

Detector and the Imaging Plane

Referring now to FIG. 6A, the stationary multisource X-ray CT imaging system 300 may also include a detector 308 (e.g. a flat panel detector) such as an amorphous silicon detector (250 mm×200 mm) with 0.12-mm native pixels, and 7.5 fps at full resolution and 30 fps in the 2×2 binning mode. At 30 fps, the short scan times may be enabled by the stationary source albeit at reduced resolution. Alternative detectors may have 0.075-mm to 0.3-mm native pixels at 26-86 fps. With full resolution at 26 fps (about 38 ms/frame for 15 frames=0.58 s detector download time), the stationary source would yield a scan time (150 mAs exposure, or 0.75 s total exposure time) of 0.58 s+0.75 s=1.33 s, a value to minimize patient motion artifacts. The flat-panel detector electronics may provide a 5-V transistor-transistor logic (TTL) pulse, which may be integrated with the source controller to synchronize firing each individual source element 303-305 of the stationary multi-X-ray source array 302.

As illustrated in FIG. 6A, by producing a multi-X-ray source array 302 with 3 focal spots (or alternately, with focal spots at the upper and lower positions), 3 images from 3 different cone angles 310 could be acquired in rapid sequence. The rotation of the CT scanner in FIG. 6A is in and out of the plane of the page, as illustrated with arrow 312. Cone angle artifacts are extremely prevalent in flat-panel based cone beam CT applications, and are produced because the object is not interrogated by all necessary angles to achieve a proper image reconstruction. The ability to rapidly pulse and hence image the object at 3 different cone angles 310 would fill in missing data, completing Fourier space, and allowing nearly ideal 3-D image reconstruction.

FIG. 6B illustrates the stationary multisource X-ray CT imaging system 300 (e.g. cone beam CT system) from the top view, relative to FIG. 6A. That is, the top view of the system shown in FIG. 6A is illustrated in FIG. 6B. The iso-center defines the center of the rotational axis, which corresponds to the vertical line 314 illustrated in FIG. 6A.

Figure 7A:
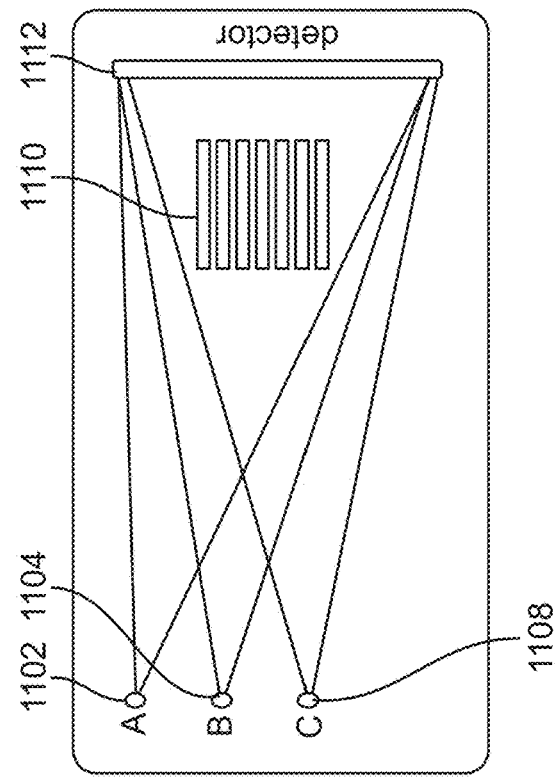
FIG. 7A-7D illustrate an experimental setup and experiment results emulating use of a stationary multisource X-ray computer tomography imaging system, according to various embodiments.

FIGS. 7A-7D illustrate an experimental setup and data received from the experimental setup from emulating the CT scanner with rotating anode approach depicted in FIGS. 6A-6B. FIG. 7A illustrates the experimental setup of an exemplary Defriese phantom 1110, which is formed of a stack of discs separated by foam spacers. The phantom 1110 is imaged on a cone beam CT system designed for breast imaging. The vertical position of the x-ray tube can be adjusted on the scanner using a computer-controlled motor. In the acquisition geometry illustrated in FIG. 7A, the x-ray source is located in three different positions, position A 1102, position B 1104, and position C 1106 at a predetermined distance from the detector 1112. The exemplary geometry illustrated in FIG. 7A simulates the capabilities of a three source x-ray tube, as illustrated in FIG. 6A, for cone beam CT imaging applications.

Figure 7C:
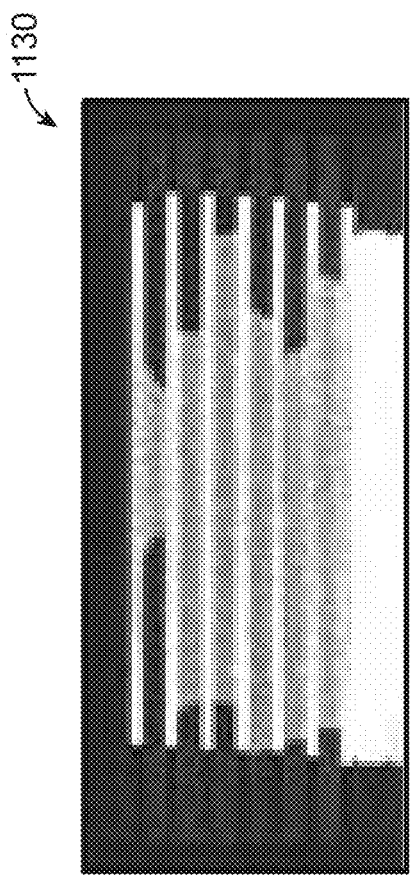
Figure 7B:
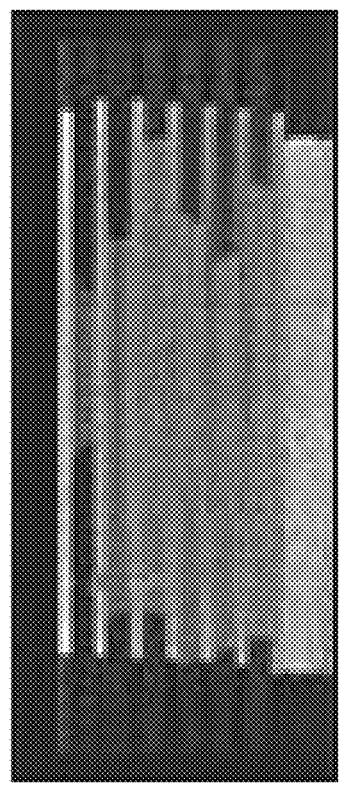
Figure 7D:
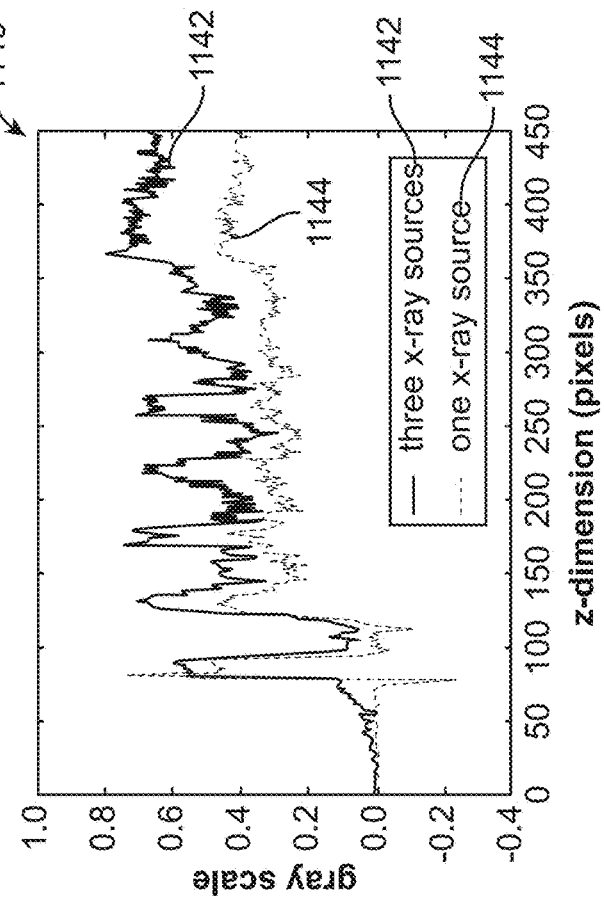

FIG. 7B illustrates an image 1120 of the Defriese phantom with the vertical dimension being the Z axis, as illustrated in FIG. 7A. FIG. 7B was acquired using only source position A 1102. FIG. 7C illustrates the Defriese phantom image 1130 using a combination of all three source locations source positions (position A 1102, position B 1104, and position C 1106). When the images 1120 and 1130 are compared, the contrast of the disks is more easily visualized in FIG. 7C compared to FIG. 7B. FIG. 7D illustrates a plot 1140 of the contrast of the disks from FIG. 7B shown with graph 1144 and FIG. 7C shown with graph 1142, illustrating that much greater contrast from FIG. 7C, where cone beam artifacts are reduced due to the multiple source positions.

The utility of a stationary multisource X-ray imaging system for cone beam CT is illustrated in FIGS. 7A-7D. In cone beam CT, the object data is under-sampled due to the single location of the x-ray source with respect to the cone angle (vertical dimension in FIG. 7A). By distributing a number of x-ray sources along the cone angle dimension, better sampling can be achieved and cone beam artifacts can be reduced. This is illustrated by comparing FIG. 7B with FIG. 7C. One of ordinary skill in the art will appreciate that the exemplary illustration provided in FIGS. 7A-7D is a physical simulation of a three-source x-ray tube, and that more sources would achieve even better performance for cone beam artifact reduction in cone beam CT systems.

Figure 8A:
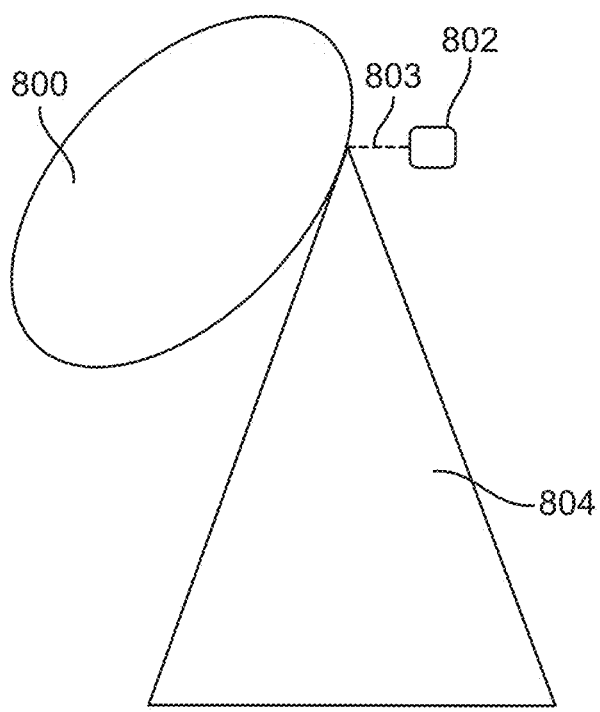
FIGS. 8A-8B illustrate how different X-ray pulse timing sequences can be used to stagger the position of the focal spot relative to the imaging plane, according to various embodiments.
Figure 8B:
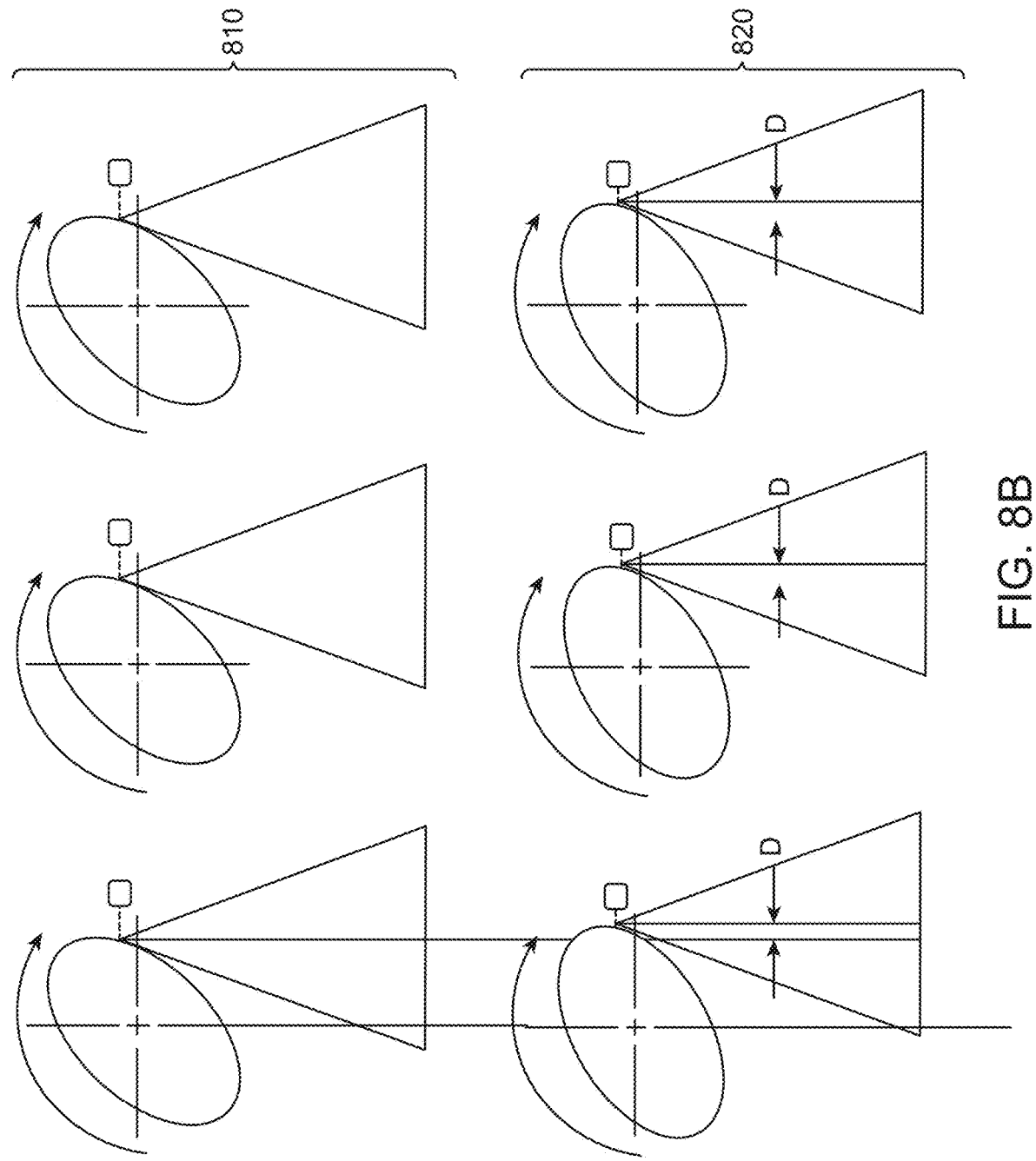

FIGS. 8A-8B illustrate using different X-ray pulse timing sequences to stagger the position of the focal spot relative to the imaging plane according to various embodiments. Pulsing the X-ray tube with precise temporal control may involve the use of a grid surrounding the cathode, and allowing relatively low voltages (e.g. 1000 V) to control the flow of electrons across the cathode-anode distance, where a much higher voltage is applied (25-150 kV).

FIG. 8A demonstrates the overall concept. The rotating anode 800 is interrogated by the pulsed electron beam 803 from the grid pulsed cathode system 802. When the electrons hit the anode material, the X-ray beam 804 is formed. The elliptical anode shaft 800 is rotating at a high rate, about 3000 to 10,000 rpm. By tracking the rotation angle, and only pulsing the electron beam 803 during a certain phase angle of anode rotation, the X-ray beam 804 is produced in the geometry illustrated in FIG. 8A. To maintain the focal spot location during an image sequence (as commonly done in tomosynthesis or CT imaging), the time between pulses would be exactly the time it takes the anode shaft to rotate 360° (referred as "T"), and thus a series of pulses could be performed at any integral multiples of T, for instance T, 2T, 3T, . . . nT.

FIG. 8B illustrates various X-ray pulses at a given phase angle producing various X-ray beams located at the same position in space. The top series of figures 810 in FIG. 8B illustrate 3 X-ray pulses at a given phase angle, producing 3 X-ray beams located at the same position in space. The bottom series of figures 820 in FIG. 8B illustrate pulsing at a slightly different phase angle, and hence the location of the focal spot (in the horizontal direction) is translated a distance D, relative to the figures 810 on the top row of FIG. 8B. This shift by a distance D can have significant utility for oversampling in many imaging scenarios.

Figure 9A:
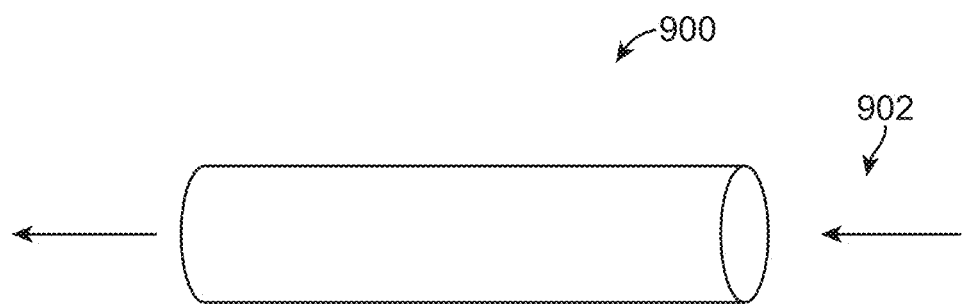
FIGS. 9A-9E illustrate various alternate designs of the rotating anode, according to various embodiments.
Figure 9B:
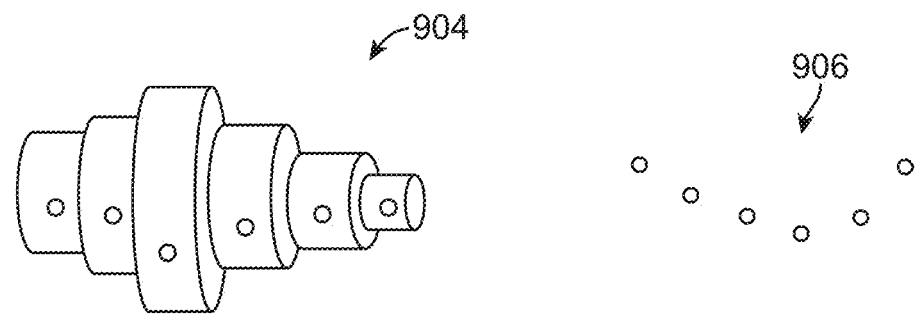
Figure 9C:
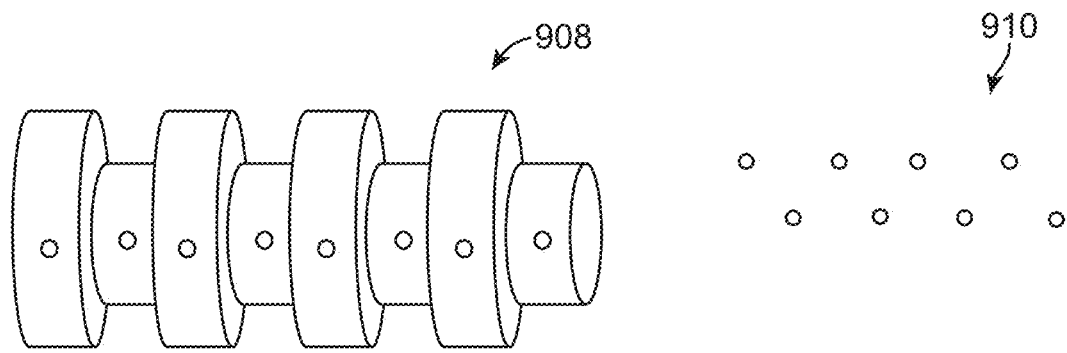

FIGS. 9A-9C illustrate alternative designs for the rotating anode. For example, as illustrated in FIG. 9A, the anode cylinder 900 may have a liquid metal or other coolant fluid 902 running through the cylinder as the anode rotates, for improving overall heat capacity. As illustrated in FIG. 9B, the cylinder 904 may have a variable diameter along its length, allowing for staggering the multi-X-ray source array in the orthogonal direction. A focal spot pattern 906 as seen from below is illustrated in FIG. 9B. FIG. 9C illustrates a cylinder design 908 similar to the one illustrated in FIG. 7A. In the embodiment illustrated in FIG. 9C, the variable diameter is used to generate two lines of sources. A focal spot pattern 910 as seen from below is illustrated in FIG. 9C.

Figure 9D:
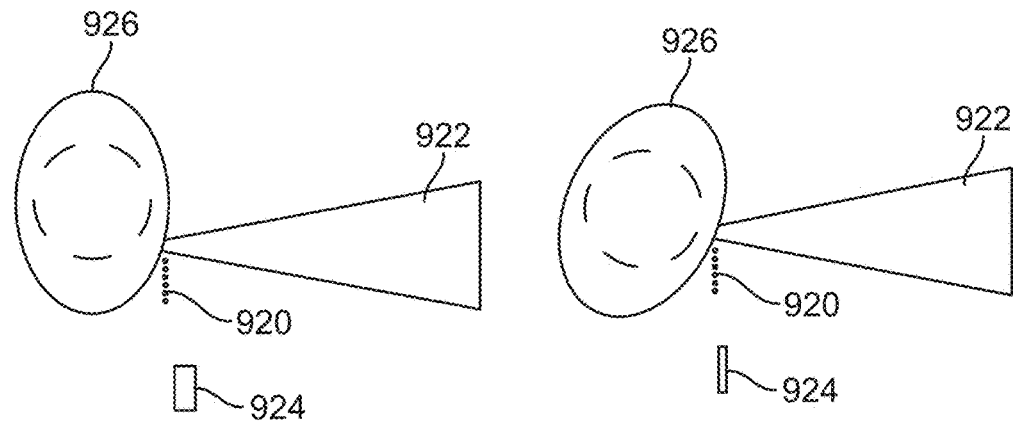

FIG. 9D illustrates an alternative design for the rotating anode where the anode drum 926 is not perfectly circular in cross section. By using elliptical sections, with proper pulsing and anode rotation rate, different focal spot sizes may be generated due to variable line-focus angles. This design could also be used to purposefully cause travel of the apparent source during anode rotation. The rotating anode 926 is interrogated by the pulsed electron beam 920 from the grid pulsed cathode system 924. When the electrons hit the anode material, the X-ray beam 922 is formed. The elliptical anode shaft 926 may rotate at a high rate, about 3000 to 10,000 rpm. By tracking the rotation angle, and only pulsing the electron beam 920 during a certain phase angle of anode rotation, the X-ray beam 922 is produced in the geometry illustrated in FIG. 9D.

Figure 9E:
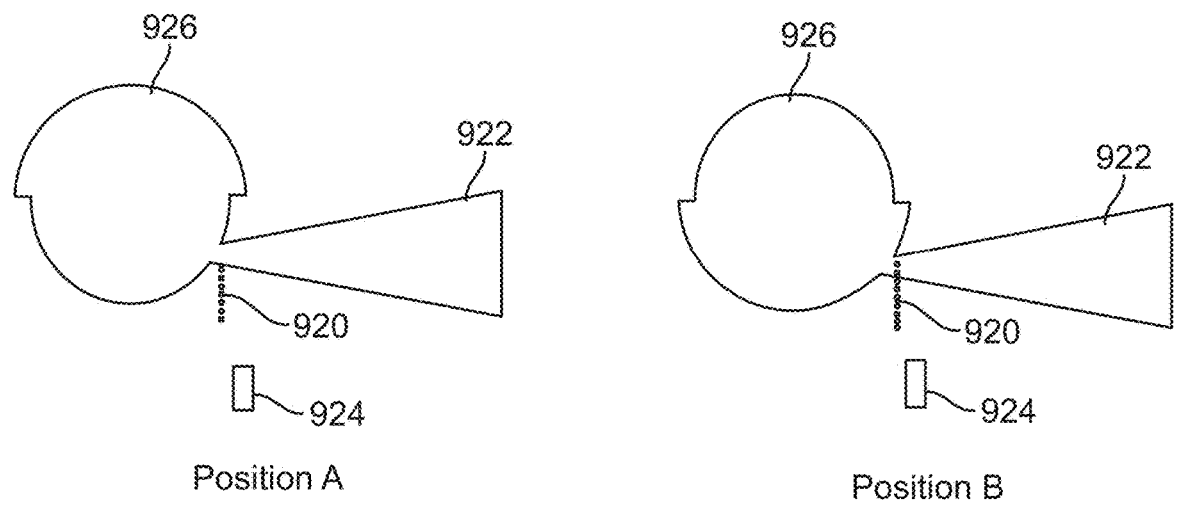

FIG. 9E illustrates an alternative design for the rotating anode where slight differences in anode diameter are used to toggle the focal spot up and down spatially, creating a "flying focal spot" with simple mechanical rotation instead of magnetic steering coils (and necessary logic). In this embodiment, the mechanical rotation is already used for the rotating anode.

Figure 10:
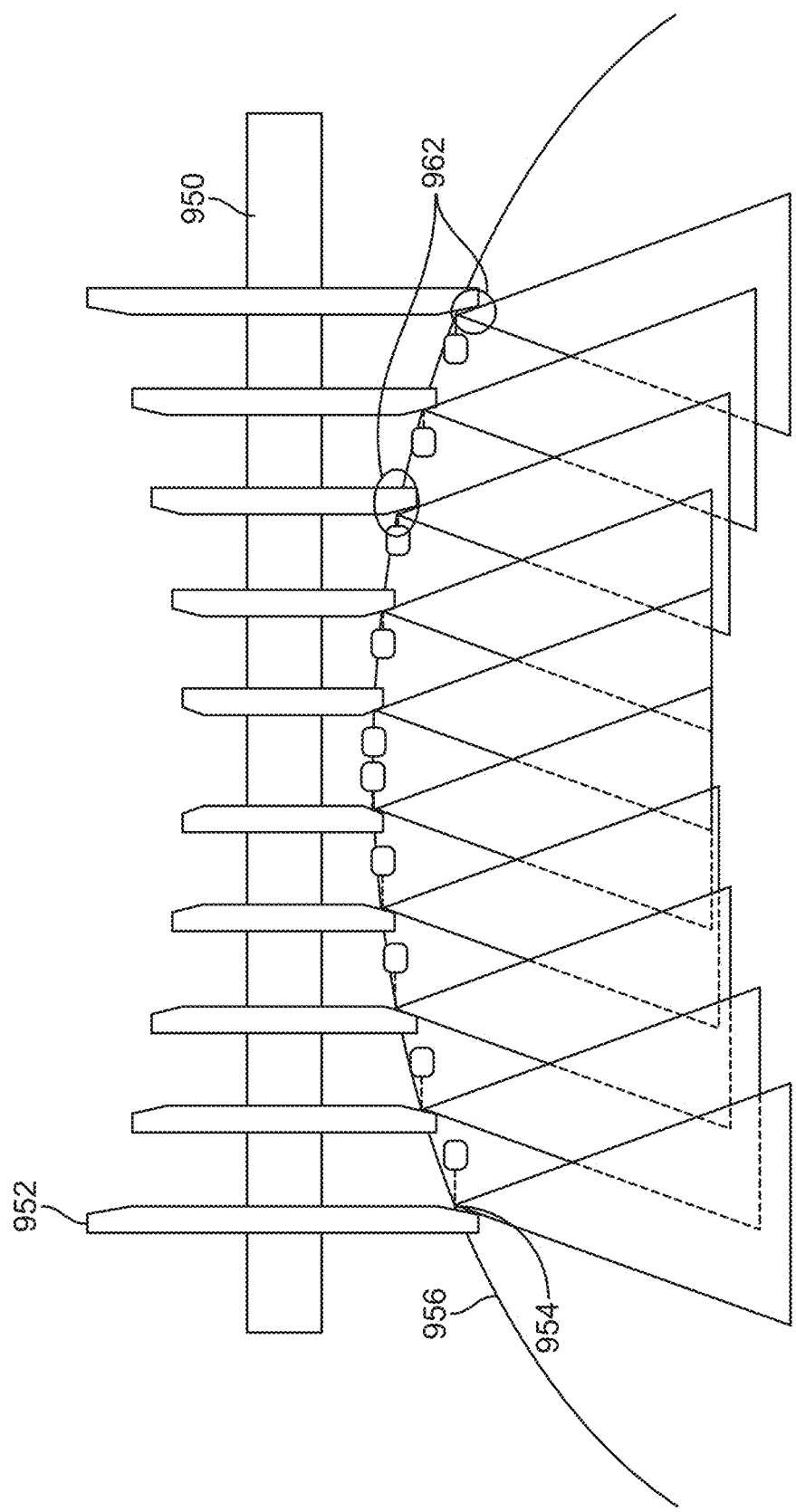
FIG. 10 illustrates an exemplary multi-X-ray source rotating anode in a tomosynthesis or other limited angle tomography imaging system, according to various embodiments.

FIG. 10 illustrates the potential of a multi-X-ray source array to function in a tomosynthesis or other limited angle tomography imaging system. The multi-source X-ray array may have focal spots 954 along the long axis of the rotating anode shaft 950 to be displaced using different diameter disks 952, such that the source distribution falls along a radius of curvature 956 to an appropriate detector system. Also, the focal spots 954 are positioned to be facing the inner side of the curve 956. In addition, the anode angles 962 of each of the disks 952 may be adjusted to deliver optimal focal spot size (i.e. image resolution) for an object located near or above the center of curvature.

By adjusting the diameter of the 10 anode disks 952 illustrated in FIG. 10, an effective radius of curvature may be achieved to equalize the X-ray beam angles and intensities in tomosynthesis imaging. This geometry has other important benefits as well. As illustrated on the left side of FIG. 10, the focal spots 954 are on the right side of the anode disks 952. However, on the right side of FIG. 10, the focal spots 954 are on the left side of the anode disks 952. This allows the trade-off between X-ray field coverage (which is a function of anode angle) and the X-ray focal spot location, which would be useful in optimizing spatial resolution by minimizing the effective spot size. Another important aspect is that the anode angles 962 of each of the anode disks 952 in this array may be different, allowing a uniform projected X-ray spot dimension to be used throughout the entire pulse sequence for an object at the center of the field-of-view. It should be noted that while the radius of curvature may have a vertex at the center of the detector, other curved shapes may provide similar functionality and not necessarily be aligned along the great circle.

Non-Medical Use Case

Embodiments of the present invention may be used (or otherwise implemented) in non-medical systems as well. For example, a stationary source CT system may be used in the screening of packages, such as carry-on bags of airline passengers.

Conventional CT systems generate tomographic data sets by mechanically rotating the X-ray source and detector assembly about the object to be imaged. This motion requires sophisticated mechanical and electrical components that have high up-front and maintenance costs. The high cost associated with these systems inhibits the use of X-ray CT for carry-on baggage screening at passenger checkpoints at, for example, airports, train stations, bus stations, etc. In conventional security imaging applications, such as carry-on luggage screening, only about 30 projections per scan are required to produce a CT data set that is adequate for inspection purposes. This is a small number compared to the about 2000 projections necessary for diagnostic medical CT. The far fewer number of projections required for carry-on luggage screening means that a simple, reliable, and therefore affordable stationary source CT system can be used.

Figure 11A:
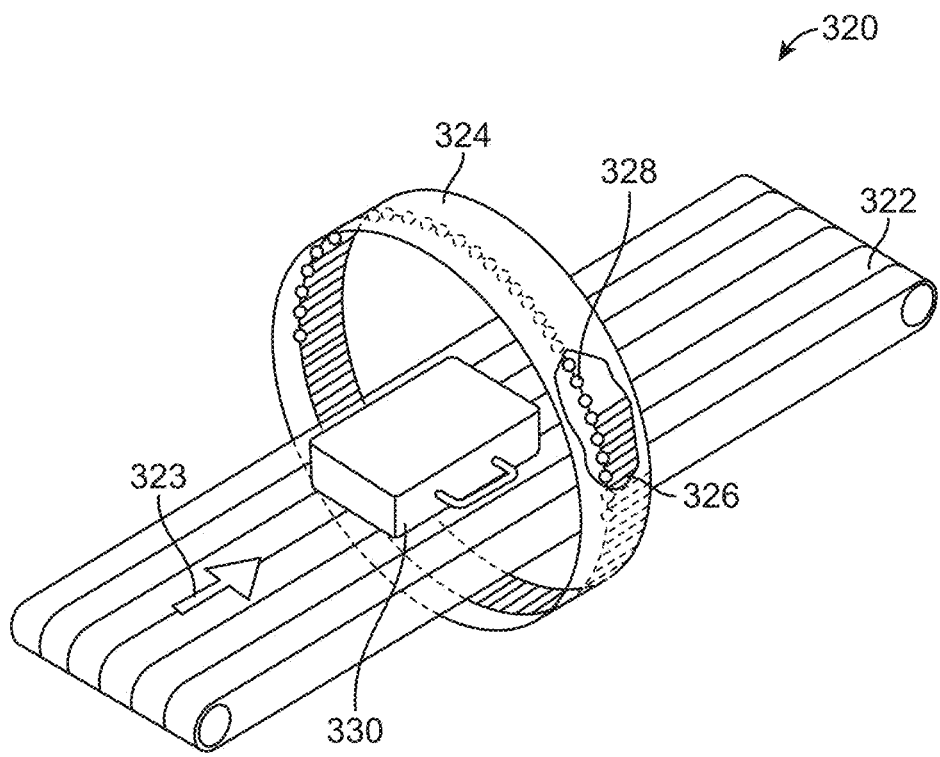
FIGS. 11A-11B illustrate an exemplary stationary multisource X-ray imaging system for package screening, according to various embodiments.
Figure 11B:
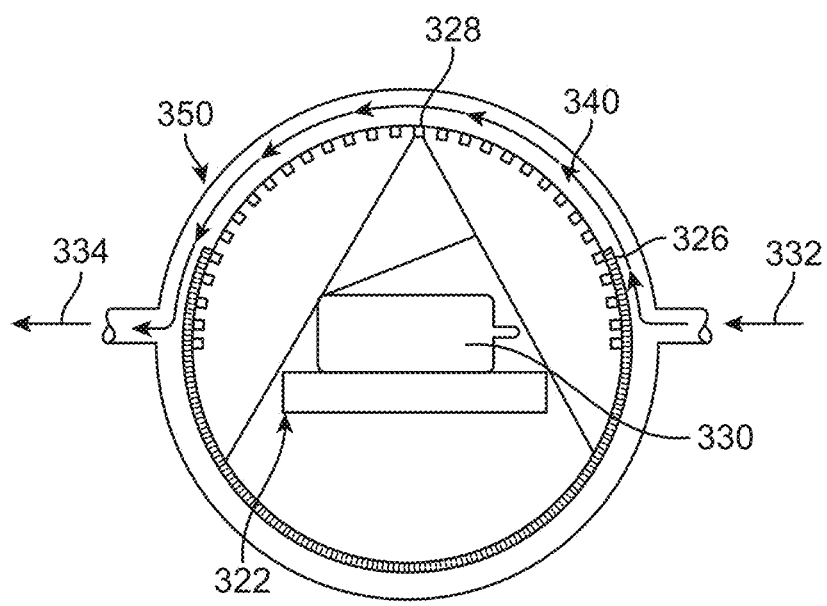

FIGS. 11A-11B illustrate an exemplary stationary multisource X-ray imaging system for package (e.g. carry-on baggage) screening at, for example, passenger checkpoints at the airports. The exemplary stationary multisource X-ray imaging system 320 may include a conveyor belt 322 where packages such as carry-on bags 330 may be placed and an imaging component 324 provided at least around an upper surface of the conveyor belt 322. The conveyor belt 322 may move in a direction 323 such that the carry-on bags 330 placed thereon move under the imaging component 324. The imaging component 324 may include a plurality of stationary X-ray source elements 328 provided over the conveyor belt 322. For example, the imaging component 324 may have a circular shape, and the plurality of stationary X-ray source elements 328 may be coupled to the portion of the imaging component 324 provided over the conveyor belt 322. As a carry-on bag 330 moves through the stationary multisource X-ray imaging system 320, individually addressable X-ray source elements 328 work in concert with a stationary ring of detectors 326 to acquire full 3D CT data sets.

The plurality of stationary X-ray source elements 328 may include a stationary array of approximately 30 individual X-ray source elements (tubes) distributed in space over 180° at 6° centers, providing a fine projection increment. The plurality of stationary X-ray source elements 328 may be provided opposite from a stationary array of detectors 326 covering 240° (i.e. 180° plus the 60° fan angle of the sources 328) providing sufficient coverage for the implementation of full three-dimensional (3D) CT reconstructions. As the carry-on bags 330 move through the exemplary stationary multisource X-ray imaging system 320 on the conveyor belt 322, the individual source elements 328 are fired sequentially, with the firing of all the plurality of stationary X-ray source elements 328 completing a single scan. Approximately 8 scans per one carry-on bag 330 may generate the complete CT data set. According to various embodiments, a given carry-on bag 330 may be imaged in less than 3 seconds. That is, about 600 bags may be scanned per hour (e.g. 3 s/bag=1200 bags/h plus about 3 s/bag for reconstruction time, automated threat identification, and operator interpretation would result in 600 bags/h).

As illustrated in FIG. 11B, the stationary multisource X-ray imaging system 320 may include a water-cooling system 350 that is shared among the plurality of stationary X-ray source elements 328. The water-cooling system 350 may provide an inlet 332 for the cooling water to enter the stationary multisource X-ray imaging system 320, a flow path 340 for the cooling water to flow therein (such that the flow path 340 is along the plurality of stationary X-ray source elements 328) and an outlet 334 for the cooling water to exit the stationary multisource X-ray imaging system 320. The water-cooling system and dielectric fluid for high-voltage insulation enable low-cost X-ray source elements 328 to be easily replaced in the field to reduce both downtime and maintenance costs.

Figure 11C:
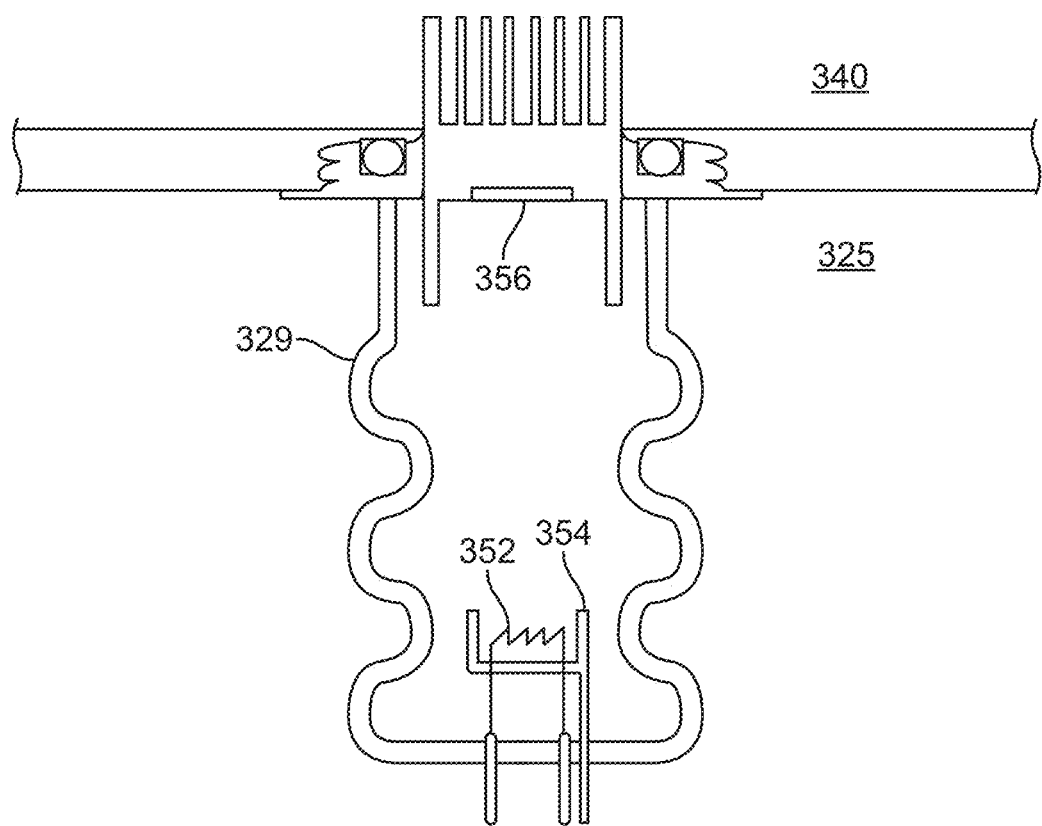
FIG. 11C illustrates an exemplary field-replaceable X-ray source element (e.g. tube) with a water-cooling system and dielectric insulating liquid, according to various embodiments.

FIG. 11C illustrates an exemplary field-replaceable X-ray source element (e.g. tube) 328 that uses a water-cooling system 350 with water as coolant 340 and dielectric insulating liquid 325. The water-cooling system 350 is shared among all source elements 328.

Each X-ray source element 328 may include a compact and field-replaceable X-ray tube 329 having a tungsten filament cathode 352, a voltage-controlled focus cup grid 354 for turning on and off the source element 328 at frequencies up to 200 Hz (e.g. a frequency greater than needed for luggage imaging needs), and a water-cooled stationary anode 356. In the exemplary embodiment illustrated in FIGS. 11A-11C, the stationary anode 356 may be a non-rotating anode.

The use of an array of individual X-ray source elements as contrasted with a single source element 328 (illustrated in FIG. 11C) means that a complicated rotating anode CT X-ray tube is not needed. Instead, simple water-cooled tubes can supply sufficient X-ray flux for high-speed CT imaging. For example, a typical abdominal CT scan, representative of what would be required for a high-quality CT image of a carry-on bag, requires an exposure of roughly 100 mAs. When a total imaging time of 3 s/bag and an 80 mm X-ray beam width at the scanner isocenter (medical CT scanners use up to 160 mm beam widths) is used, then over the length of a carry-on bag (e.g. about 600 mm maximum), (600 mm/bag)/(80 mm/scan)=(7.5 scans/bag) would yield to (3 s/bag)/(7.5 scans/bag)=(0.4 s/scan). With 30 source elements/scan, the on-time of each element would be (0.4 s/scan)/(30 elements/scan)=(13 ms/element). Accordingly, each source element would operate at (100 mAs)/(0.4 s)=250 mA. Given that the source element on-times are short (e.g. about 13 ms) and separated by relatively long off-times (e.g. about 0.4 s between scans), a stationary water-cooled anode is sufficient to prevent anode damage due to beam heating with an effective 1 to 2 mm focal spot size. The above described system may be used during 24 h/day-7 day/week duty cycle required for passenger checkpoint baggage screening.

Dual-energy imaging to better identify the density and atomic number (Z) of the objects within the bag may be implemented by: 1) accumulating images at different energies by pulsing the beam energy of the X-ray source elements 328 (e.g. two acquisition modes); 2) using a sandwiched detector configuration, wherein two detector arrays are separated by, for example a metal sheet acting as an energy filter (e.g. single image acquisition mode); or 3) using 60 X-ray source elements with 30 X-ray source elements operating at low energy and 30 X-ray source elements at high energy (e.g. two acquisition modes).

Advantages of the individual, and therefore the array of, X-ray source element tubes include 1) the water-cooling structure and hardware are shared among all source elements; 2) the source elements are simple due to a stationary anode and small because high-voltage insulation is implemented in a dielectric fluid bath, again shared among all tubes; 3) all elements use the same X-ray generator power supply; and 4) the source elements are individually plugged into a water-cooled 180° ring and therefore are easily field-replaceable, thereby reducing maintenance costs and downtime.

The stationary multisource X-ray imaging system described herein may also include key electronics components such as a high-voltage power supply, a source-control circuit to operate the tungsten filament cathodes and turn them on and off sequentially, and a circuit for multiplexing cathode operation with the detector. A standard X-ray generator supply (35-160 kV) may be employed to power the high voltage for the stationary source.

Control System

Figure 12:
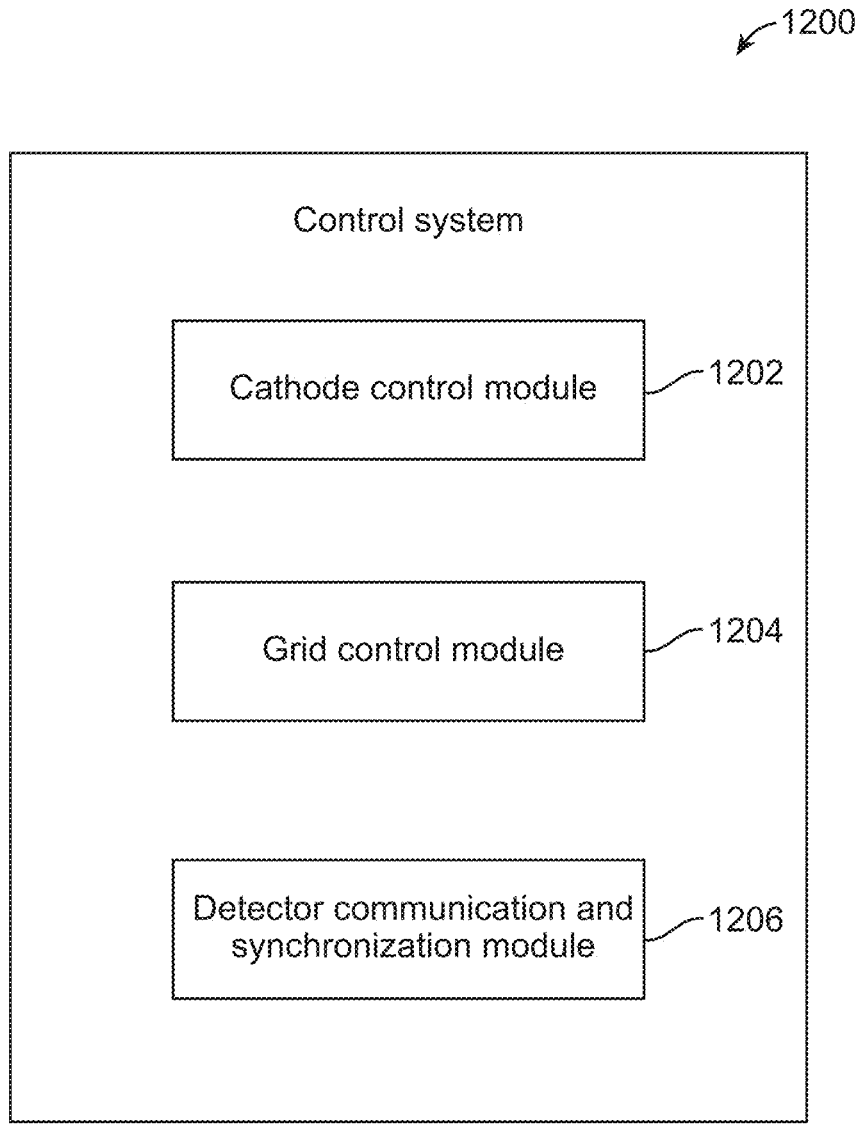
FIG. 12 illustrates an exemplary control system, according to various embodiments.

The control system for the stationary source and/or the detector may include subsystems or components that are shown in FIG. 12. The source control system 1200 may include, among other modules, a cathode control module 1202, a grid (i.e., electron beam) control module 1204, and a detector communication and synchronization module 1206. The control system 1200 may fire the stationary source with variable pulse widths and times between pulses. The time between pulses may be controlled by synchronization with the detector.

The cathode control module 1202 may regulate the current and voltage applied to each cathode by feedback to keep the temperature (i.e., emission current) of each cathode constant at a value that can be set by a system operator depending on the X-ray exposure and/or exposure time required. The cathode control module 1202 may maintain emission currents stable to levels of <0.1% over many hours. As a result, the emission current from each cathode comprising the stationary source may be precisely regulated and thereby current variations between the source elements may be prevented, or imposed (e.g., to make up for small differences in source-to-object distance (SOD)).

The grid control module (i.e. electron beam control module) 1204 may be control governed by the focus-cup grid electrode voltages to (1) control of the beam size on the anode; and (2) modulate the beam "on" and "off." Each individual multi-X-ray source array element may have an independent controller for its focus-cup grid voltage. When the source element is "on," the focus-cup grid voltage may be held at a particular forward bias such that the electrons reach the anode. The bias may be predetermined by parameterization with the size of the X-ray focal spot for a given anode voltage using a pinhole camera to measure the X-ray focal spot geometry. Modulation of the X-ray beam from each individual source may include switching its focus-cup-grid voltage from the biased "on" state to the biased "off" state. The "off" state may require the application of about 2 kV to the focus-cup grid. High-voltage MOSFET transistors may be used to apply these voltages, and electron (i.e., X-ray) pulses from each individual source element can be provided in a range of 5 ms to 0.2 s.

The detector communication and synchronization module 1206 may include electronics associated with the flat-panel detector that provide a 5 V transistor-transistor-logic (TTL) pulse for each frame. The TTL pulse may be integrated with the focus-cup-grid voltage on each individual multi-X-ray source array to synchronize their firing.

As provided above, the anode may be driven by an induction motor. The motor drive may be integrated with the source controller such that the anode may attain the set angular velocity before the multi-X-ray source array scan is initiated.

Phase-locked synchronization strategies may be used as control logic to synchronize the output of each of the individual multi-X-ray source arrays with frame-integration on the detector. Using full frame (1×1) binning or (2×2) binning on a flat panel, 7.5 frames-per-second (fps) and 30 fps may be acquired respectively. Therefore the scan time for the stationary source with 15 multi-X-ray source array elements and a 100-mAs exposure is 15 frames/7.5 fps+100 mAs/200 mA=2.5 s at full resolution (1×1 binning) and 15 frames/30 fps+100 mAs/200 mA=1.0 s with (2×2) binning. These scan times are consistent with typical mammographic acquisition times. In some embodiments, another detector having 0.075-mm to 0.3-mm native pixels at 26-86 fps may be used. With full resolution (1×1 binning) at 26 fps, the stationary source would yield a scan time with a 100-mAs exposure of 15 frames/26 fps+100 mAs/2000 mA=1.1 s, a much shorter scan time than commercially available tomosynthesis acquisitions using mechanical source translation (see Table 1). A dedicated computer interface, developed to serve as the system console, may also receive the images generated by the flat-panel detector. After acquisition, all right images are automatically pushed to the control system via a communication network (e.g. using a dedicated Ethernet backbone).

According to various embodiments, the control system 1200 may be implemented by a computing system. The computing system may include one or more computers and/or servers (e.g., one or more access manager servers), which may be general purpose computers, specialized server computers (including, by way of example, PC servers, UNIX servers, mid-range servers, mainframe computers, rack-mounted servers, etc.), server farms, server clusters, distributed servers, or any other appropriate arrangement and/or combination thereof. The control system 1200 may run any of operating systems or a variety of additional server applications and/or mid-tier applications, including HTTP servers, FTP servers, CGI servers, Java servers, database servers, and the like. The control system 1200 may be implemented using hardware, firmware, software, or combinations thereof.

In some embodiments, the control system 1200 may be implemented by multiple computing devices (e.g., access manager servers) deployed as a cluster in a data center, which allows for scalability and high availability. Multiple such geographically dispersed data centers with access manager server clusters can be connected (wired or wirelessly) to constitute a multi-data center (MDC) system. An MDC system may satisfy high availability, load distribution, and disaster recovery requirements of access servers within an enterprise computer network. An MDC system may act as a single logical access server to support SSO services for the control system 1200.

The control system 1200 may include at least one memory, one or more processing units (or processor(s)), and storage. The processing unit(s) may be implemented as appropriate in hardware, computer-executable instructions, firmware, or combinations thereof. In some embodiments, the control system 1200 may include several subsystems and/or modules. For example, the control system 1200 may include the cathode control module 1202, the grid control module 1204 and the detector communication and synchronization module 1206. Each of these subsystems and/or modules in a, the control system 1200 may be implemented in hardware, software (e.g., program code, instructions executable by a processor) executing on hardware, or combinations thereof. In some embodiments, the software may be stored in a memory (e.g., a non-transitory computer-readable medium), on a memory device, or some other physical memory and may be executed by one or more processing units (e.g., one or more processors, one or more processor cores, one or more GPUs, etc.). Computer-executable instructions or firmware implementations of the processing unit(s) may include computer-executable or machine-executable instructions written in any suitable programming language to perform the various operations, functions, methods, and/or processes described herein. The memory may store program instructions that are loadable and executable on the processing unit(s), as well as data generated during the execution of these programs. The memory may be volatile (such as random access memory (RAM)) and/or non-volatile (such as read-only memory (ROM), flash memory, etc.). The memory may be implemented using any type of persistent storage device, such as computer-readable storage media. In some embodiments, computer-readable storage media may be configured to protect a computer from an electronic communication containing malicious code. The computer-readable storage media may include instructions stored thereon, that when executed on a processor, perform the operations described herein.

The control system 1200 may communicate with the detector and/or the stationary source via one or more communication networks. Examples of communication networks may include a mobile network, a wireless network, a cellular network, a local area network (LAN), a wide area network (WAN), other wireless communication networks, or combinations thereof.

Embodiments provide a reliable X-ray imaging system including stationary tungsten filament cathodes as X-ray source and a rotating anode. The system yields short scan time to reduce blurring due to patient motion. The system incorporates several unique imaging modalities such as single-scan, dual-energy imaging for morphology and vascular enhancement information as with dynamic, contrast-enhanced MRI.

The above description is illustrative and is not restrictive. Many variations of the invention may become apparent to those skilled in the art upon review of the disclosure. The scope of the invention may, therefore, be determined not with reference to the above description, but instead may be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. An X-ray imaging system comprising:
   a stationary source including:
      at least one stationary multi-X-ray source array including a plurality of cathodes,
      an anode rotating about a first axis, wherein the anode is stationary with respect to a second and third axes perpendicular to the first axis,
      a control grid provided between the anode and the at least one stationary multi-X-ray source array, wherein the control grid includes a plurality of focusing cups corresponding to a plurality of focal spots formed on an exterior surface of the anode, wherein the plurality of focusing cups are configured to direct electrons emitted by the plurality of cathodes toward the plurality of focal spots of the anode to generate X-rays;
   a stationary detector positioned across from the stationary source, wherein projections of an object imaged using the X-ray imaging system are formed on the stationary detector; and
   a control system programmed to:
      control the stationary source to synchronize firing of at least a first set of the plurality of cathodes at a first time and synchronize firing of at least a second set of the plurality of cathodes at a second time based on a predetermined sequence determined as a function of a rotation angle of the anode,
      acquire the projections from the stationary detector, and
      reconstruct a 3-D image of the object using the projections acquired from the stationary detector.

2. The X-ray imaging system of claim 1, further comprising:
   an inner flow chamber in form of a rifled tube provided within and extending along the anode, wherein spiral scoring is formed on an interior surface of the inner flow chamber and a coolant circulates in the inner flow chamber to carry heat away from the anode.

3. The X-ray imaging system of claim 1, wherein the anode includes a rotating shaft and a plurality of discs coupled to the rotating shaft.

4. The X-ray imaging system of claim 1, wherein the anode includes an elliptical rotating shaft.

5. The X-ray imaging system of claim 1, wherein the control system is further programmed to fire the first set of the plurality of cathodes and the second set of the plurality of cathodes with variable pulse widths.

6. The X-ray imaging system of claim 1, wherein heat distribution in the anode is controlled using the predetermined sequence.

7. The X-ray imaging system of claim 1 wherein the plurality of cathodes include at least one thermionic cathode.

8. The X-ray imaging system of claim 1, further comprising:
   a collimator for collimating X-rays generated when electrons emitted by the at least one stationary multi-X-ray source array contact the anode; and
   a filter coupled to the collimator for filtering the X-rays collimated by the collimator.

9. The X-ray imaging system of claim 1, wherein the anode includes a rotating shaft rotating about the first axis, and a plurality of discs coupled to the rotating shaft.

10. The X-ray imaging system of claim 9, wherein at least two of the plurality of discs have different diameters.

11. The X-ray imaging system of claim 1, further comprising:
    an inner flow chamber provided within the anode, wherein a coolant circulates in the inner flow chamber to carry heat away from the anode.

12. The X-ray imaging system of claim 11, wherein a plurality of grooves are formed on an exterior surface of the inner flow chamber of the anode.

13. The X-ray imaging system of claim 1, wherein a first cathode among the plurality of cathodes forms a first projection of the object from a first angle, and a second cathode among the plurality of cathodes forms a second projection of the object from a second angle different than the first angle.

14. The X-ray imaging system of claim 1, wherein the plurality of focal spots are staggered in position.

15. The X-ray imaging system of claim 1, wherein the plurality of focal spots are staggered in shape.

16. An X-ray imaging system comprising:
    a stationary source including:
       at least one stationary multi-X-ray source array, wherein the stationary multi-X-ray source array includes a plurality of cathodes, and
       an anode including a rotating shaft rotating about a first axis at varying phase angles, wherein the anode is stationary with respect to a second and third axes perpendicular to the first axis; and
    a control system for controlling the stationary source to synchronize firing of at least a first set of the plurality of cathodes at a first phase angle of the anode and synchronize firing of at least a second set of the plurality of cathodes at a second phase angle of the anode.

17. The X-ray imaging system of claim 16, wherein the rotating shaft is an elliptical shaft.

18. The X-ray imaging system of claim 16, wherein the rotating shaft is in shape of a rotating pin.

19. The X-ray imaging system of claim 16, wherein focal spots generated by anode rotation are staggered in position or in shape.

20. A method for controlling an X-ray imaging system including at least one stationary multi-X-ray source array, wherein the stationary multi-X-ray source array includes a plurality of cathodes, and an anode rotating about a first axis, wherein the anode is stationary with respect to a second and third axes perpendicular to the first axis, and a stationary detector positioned across from the at least one stationary multi-X-ray source array, wherein projections of an object imaged using the X-ray imaging system are formed on the stationary detector, the method comprising:
- synchronizing firing of at least a first set of the plurality of cathodes at a first time and synchronize firing of at least a second set of the plurality of cathodes at a second time based on a predetermined sequence determined as a function of a rotation angle of the anode;
- acquiring the projections from the stationary detector; and
- reconstructing a 3-D image of the object using the projections acquired from the stationary detector.

* * * * *